(12) United States Patent
Campbell et al.

(10) Patent No.: US 7,786,163 B2
(45) Date of Patent: Aug. 31, 2010

(54) CONSTRAINED CYANO COMPOUNDS

(75) Inventors: David Alan Campbell, San Diego, CA (US); Juan Manuel Betancort, San Diego, CA (US); David T. Winn, San Diego, CA (US)

(73) Assignee: Forest Laboratories Holdings Limited (BM)

( * ) Notice: Subject to any disclaimer, the term of this patent is extended or adjusted under 35 U.S.C. 154(b) by 1420 days.

(21) Appl. No.: 11/179,797

(22) Filed: Jul. 12, 2005

(65) Prior Publication Data

US 2006/0009518 A1 Jan. 12, 2006

Related U.S. Application Data

(60) Provisional application No. 60/587,391, filed on Jul. 12, 2004.

(51) Int. Cl.
*A61K 31/407* (2006.01)
*C07D 513/04* (2006.01)

(52) U.S. Cl. ........................ 514/413; 548/453
(58) Field of Classification Search ............... 514/522, 514/413; 558/410; 548/453
See application file for complete search history.

(56) References Cited

U.S. PATENT DOCUMENTS

| | | | |
|---|---|---|---|
| 3,983,140 A | 9/1976 | Endo et al. | |
| 4,027,009 A | 5/1977 | Grier et al. | |
| 4,231,938 A | 11/1980 | Monaghan et al. | |
| 4,346,227 A | 8/1982 | Terahara et al. | |
| 4,379,785 A | 4/1983 | Weyer et al. | |
| 4,448,784 A | 5/1984 | Glamkowski et al. | |
| 4,450,171 A | 5/1984 | Hoffman et al. | |
| 4,572,912 A | 2/1986 | Yoshioka et al. | |
| 4,639,436 A | 1/1987 | Junge et al. | |
| 4,681,893 A | 7/1987 | Roth | |
| 4,759,923 A | 7/1988 | Buntin et al. | |
| 4,871,721 A | 10/1989 | Biller | |
| 4,904,769 A | 2/1990 | Rauenbusch | |
| 4,924,024 A | 5/1990 | Biller | |
| 5,006,530 A | 4/1991 | Angerbauer et al. | |
| 5,011,930 A | 4/1991 | Fujikawa et al. | |
| 5,177,080 A | 1/1993 | Angerbauer et al. | |
| 5,260,440 A | 11/1993 | Hirai et al. | |
| 5,273,995 A | 12/1993 | Roth | |
| 5,346,701 A | 9/1994 | Heiber et al. | |
| 5,354,772 A | 10/1994 | Kathawala | |
| 5,385,929 A | 1/1995 | Bjorge et al. | |
| 5,447,954 A | 9/1995 | Gribble et al. | |
| 5,488,064 A | 1/1996 | Sher | |
| 5,491,134 A | 2/1996 | Sher et al. | |
| 5,541,204 A | 7/1996 | Sher et al. | |
| 5,594,016 A | 1/1997 | Ueno et al. | |
| 5,595,872 A | 1/1997 | Wetterau, II et al. | |
| 5,614,492 A | 3/1997 | Habener | |
| 5,631,224 A | 5/1997 | Efendic et al. | |
| 5,686,104 A | 11/1997 | Mills et al. | |
| 5,712,279 A | 1/1998 | Biller et al. | |
| 5,712,396 A | 1/1998 | Magnin et al. | |
| 5,739,135 A | 4/1998 | Biller et al. | |
| 5,760,246 A | 6/1998 | Biller et al. | |
| 5,770,615 A | 6/1998 | Cheng et al. | |
| 5,776,983 A | 7/1998 | Washburn et al. | |
| 5,827,875 A | 10/1998 | Dickson, Jr. et al. | |
| 5,885,983 A | 3/1999 | Biller et al. | |
| 5,952,322 A | 9/1999 | Hoover et al. | |
| 5,962,440 A | 10/1999 | Sulsky | |
| 5,998,463 A | 12/1999 | Hulin et al. | |
| 6,124,305 A | 9/2000 | Villhauer | |
| 6,271,232 B1 | 8/2001 | Campbell et al. | |
| 7,094,800 B2 * | 8/2006 | Schoenafinger et al. | 514/413 |

FOREIGN PATENT DOCUMENTS

| | | |
|---|---|---|
| EP | 0818448 | 6/1997 |
| EP | 0978279 | 7/1999 |
| EP | 1041068 | 3/2000 |
| WO | WO 96/38144 | 12/1996 |
| WO | WO 96/39384 | 12/1996 |
| WO | WO 96/39385 | 12/1996 |
| WO | WO 97/12613 | 4/1997 |
| WO | WO 97/12615 | 4/1997 |
| WO | WO 97/21993 | 6/1997 |
| WO | WO 98/19998 | 5/1998 |
| WO | WO 99/00353 | 1/1999 |
| WO | WO 99/26659 | 6/1999 |
| WO | WO 99/38501 | 8/1999 |
| WO | WO 99/43663 | 9/1999 |
| WO | WO 00/34241 | 6/2000 |
| WO | WO 00/38722 | 7/2000 |
| WO | WO 00/47206 | 8/2000 |
| WO | WO-2006017292 A1 | 2/2006 |

OTHER PUBLICATIONS

Vippagunta, et al., Crystalline solids, 2001, Advanced Drug Delivery Reviews, 48, pp. 3 and 18.*
Wolff et al., Burger's Medicinal Chemistry and Drug Discovery, 1994, Wiley-Interscience, Fifth Edition, vol. I: Principles and Practice, pp. 975-977.*
Allen, N. E. et al., "Molecular Modeling of γ-Lactam Analogues of β-Lactam Antibacterial Agents: Synthesis and Biological Evaluation of Selected Penem and Carbapenem Analogues," *Tetrahedron* (1989) vol. 45, No. 7, pp. 1905-1928; published by pergamon Press plc.
Baldwin, J. E. et al., "γ-Lactam Analogues of Penicillanic and Carbapenicillanic Acids," *Tetrahedron* (1984) vol. 40, No. 21, pp. 4513-4525; published by Pergamon Press Ltd.

(Continued)

*Primary Examiner*—Karmal A Saeed
*Assistant Examiner*—Kristin Bianchi
(74) *Attorney, Agent, or Firm*—David M. Mott

(57) ABSTRACT

Certain constrained cyano compounds are useful as inhibitors of post-proline/alanine cleaving amino-dipeptidases. Accordingly, these compounds can be employed, alone or with another therapeutic agent, to treat diabetes (especially, Type II diabetes), hyperglycemia, Syndrome X, diabetic complications, hyperinsulinemia, obesity, atherosclerosis and related diseases, as well as various immunomodulatory diseases and chronic inflammatory bowel disease.

34 Claims, No Drawings

OTHER PUBLICATIONS

Biller et al., "Squalene Synthase Inhibitors," *Current Pharmaceutical Design*, 1996, vol. 2, No. 1, pp. 1-40; published by Bentham Science Publishers B.V.

Capson, T. L., "Synthesis and Evaluation of Ammonium Analogs of Carbocationic Intermediates in Squalene Biosynthesis," 1987 Ph.D. dissertation, Univ. of Utah, SciFinder (Oct. 19, 2005).

Corey, E. J. et al., "Application of Unreactive Analogs of Terpenoid Pyrophosphates to Studies of Multistep Biosynthesis . . . ," *Journal of the American Chemical Society*, 1976, vol. 98:5, pp. 1291-1293.

Cornicelli, J. A. et al., "15-Lipoxygenase and its Inhibition: A Novel Therapeutic Target for Vascular Disease", *Current Pharmaceutical Design*, 1999, vol. 5, No. 1, pp. 11-20; published by Bentham Science Publishers B.V.

Dolbeare, K. et al., "Synthesis and Dopamine Receptor Modulating Activity of 3-Substituted γ-Lactam Peptidomimetics of L-Prolyl-L-Leucyl-Glycinamide," *J. Med. Chem.* 2003, 46, pp. 727-733; published by American Chemical Society.

Hara, S., "Ileal Na+/bile acid cotransporter inhibitors," *Drugs of the Future*, 1999, 24(4), pp. 425-430; published by Prous Science.

Gerona-Navarro, G. et al., "Entry to New Conformationally Constrained Amino Acids, First Synthesis of 3-Unsubstituted 4-Alkyl-4-carboxy-2-azetidinone Derivatives via an Intramolecular . . . ," *J. Org. Chem.* 2001, 66, pp. 3538-3547; published by American Chemical Society.

Gerona-Navarro, G. et al., "General Approach for the Stereocontrolled Construction of the β-Lactam Ring in Amino Acid-Derived 4-Alkyl-4-carboxy-2-azetidinones," *J. Org. Chem.* 2002 67, pp. 3953-3956; published by American Chemical Society.

Gerona-Navarro, G. et al., "Easy access to orthogonally protected α-alkyl aspartic acid and α-alkyl asparagine derivatives by controlled opening of β-lactams," *Tetrahedron Lett.* 2003, 44, pp. 6145-6148; published by Elsevier Ltd.

Ghiselli, G., "The Pharmacological Profile of FCE 27677: A Novel ACAT Inhibitor with Potent Hypolipidemic Activity Mediated by Selective Suppression of the Hepatic Secretion of ApoB-100-Containing Lipoprotein," *Cardiovascular Drug Reviews*, vol. 16, No. 1, 1998, pp. 16-30; published by Neva Press, Branford, CT.

Khalil, E. M. et al., "Synthesis and Dopamine Receptor Modulating Activity of Substituted Bicyclic Thiazolidine Lactam Peptidomimetics of L-Prolyl- L-leucyl-glycinamide," *J. Med. Chem.* 1999, 42, pp. 2977-2987; published by American Chemical Society.

Krause, B. R. et al., "ACAT Inhibitors: Physiologic Mechanisms for Hypolipidemic and Anti-Atherosclerotic Activities in Experimental Animals," *Inflammation: Mediators and Pathways* (1995), pp. 173-198, R. R. Ruffolo, Jr. and M. A. Hollinger, Ph.D. (eds.); published by CRC Press, Boca Raton, FL.

McClard, R. W. et al., "Novel Phosphonylphosphinyl (P-C-P-C) Analogues of Biochemically Interesting Diphosphates . . . ," *J. Am. Chem. Soc.*, 1987, 109, pp. 5544-5545; published by American Chemical Society.

Murakami, K. et al., "A Novel Insulin Sensitizer Acts As a Coligand for Peroxisome Proliferation—Activated Receptor Alpha (PPAR alpha) and PPAR gamma. Effect on PPAR alpha Activation on Abnormal Lipid Metabolism in Liver of Zucker Fatty Rats," *Diabetes*, vol. 47, Dec. 1998, pp. 1841-1847.

Nagatsu, T. et al., "New Chromogenic Substrates for X-Prolyl dipeptidyl-aminopeptidase," *Analytical Biochemistry*, vol. 74, Issue 2, Aug. 1976, pp. 466-476; published by Academic Press, Inc.

Ortiz de Montellano, P. R. et al., "Inhibition of Squalene Synthetase by Farnesyl Pyrophosphate Analogues," *Journal of Medicinal Chemistry*, 1977, vol. 20, No. 2, pp. 243-249.

Rahfeld, J. et al., "Extended Investigation of the Substrate Specificity of Dipeptidyl Peptidase IV from Pig Kidney," *Biol. Chem. Hoppe-Seyler*, May 1991, vol. 372, pp. pp. 313-318; published by Walter de Gruyter & Co.

Rosenblum, S. B. et al., "Discovery of 1-(4-Fluorophenyl)-(3R)-[3-(4-fluorophenyl)-(3S)-hydroxypropyl]-(4S)-(4-hydroxyphenyl)-2-azetidinone (SCH 58235) . . . ," *J. Med. Chem.* 1998, 41, pp. 973-980; published by American Chemical Society.

Salisbury, B. G. et al., "Hypocholesterolemic Activity of a Novel Inhibitor of Cholesterol Absorption, SCH 48461," *Atherosclerosis* 115 (1995) pp. 45-63; published by Elsevier Science Ireland Ltd.

Sendobry, S. M. et al., "Attenuation of diet-induced atherosclerosis in rabbits with a highly selective 15-lipoxygenase inhibitor lacking significant antioxidant properties," *British Journal of Pharmacology* (1997) 120, pp. 1199-1206; published by Stockton Press.

Sliskovic, D. R. et al., "ACAT Inhibitors: Potential Anti-atherosclerotic Agents," *Current Medicinal Chemistry*, 1994, vol. 1, No. 3, pp. 204-225; published by Bentham Science Publishers B.V.

Smith, C. et al., "RP 73163: A Bioavailable Alkylsulphinyl-Diphenylimidazole ACAT Inhibitor," *Bioorganic & Medicinal Chemistry Letters*, 1996, vol. 6, No. 1, pp. 47-50; published by Elsevier Science Ltd.

Trivedi, B. K. et al., "Inhibitors of Acyl-CoA: Cholesterol O-Acyl Transferase (ACAT) as Hypocholesterolemic Agents . . . ," *Chemtracts—Organic Chemistry*, 1995, vol. 8, pp. 359-362; published by Data Trace Chemistry Publishers, Inc.

\* cited by examiner

US 7,786,163 B2

CONSTRAINED CYANO COMPOUNDS

CROSS REFERENCE TO RELATED APPLICATIONS

This application claims the benefit of Campbell et al. U.S. Provisional Application No. 60/587,391, filed Jul. 12, 2004, which is hereby incorporated herein by reference in its entirety and for all purposes.

FIELD OF THE INVENTION

The present invention relates to constrained cyano compounds and to their use as selective inhibitors of post-proline/alanine cleaving amino-dipeptidases. The invention further relates to methods of employing such inhibitors, alone or with another therapeutic agent, to treat diabetes (especially, Type II diabetes), hyperglycemia, Syndrome X, diabetic complications, hyperinsulinemia, obesity, atherosclerosis and related diseases, as well as various immunomodulatory diseases and chronic inflammatory bowel disease.

BACKGROUND OF THE INVENTION

The following background commentary is an aid to understanding the present invention. Inclusion of this commentary is not an admission concerning the nature or content of the prior art.

Dipeptidyl peptidase-IV (DPP-IV) is a serine protease that belongs to the group of post-proline/alanine cleaving amino-dipeptidases. DPP-IV preferentially catalyzes the release of an N-terminal dipeptide from proteins with N-terminal penultimate proline or alanine.

The physiological roles of DPP-IV are diverse. DPP-IV is believed to play an important role in neuropeptide metabolism, T-cell activation, gastric ulceration, functional dyspepsia, obesity, appetite regulation, impaired fasting glucose (IFG), and diabetes. In particular, DPP-IV has been implicated in the control of glucose metabolism because its substrates include the insulinotropic hormones, glucagon like peptide-1 (GLP-1) and gastric inhibitory peptide (GIP), which are inactivated by removal of their two N-terminal amino acids.

In vivo administration of synthetic inhibitors of DPP-IV prevents N-terminal degradation of GLP-1 and GIP, resulting in higher plasma concentrations of these hormones, increased insulin secretion and, therefore, improved glucose tolerance. Therefore, such inhibitors have been proposed for the treatment of patients with type II diabetes, a disease characterized by decreased glucose tolerance and insulin resistance.

Post-proline/alanine cleaving amino-dipeptidases have been discovered, including DPP-VII, DPP-VIII, DPP-IX, and fibroblast activation protein (FAP), that have the substrate- and inhibitor-specificity of DPP-IV. Thus, it has become clear that inhibitors of this sort may affect multiple members of the enzyme group.

The precise physiological role of each of these post-proline/alanine cleaving enzymes is not well defined. Consequently, inhibiting each of them separately, a subset of them, or all of them at the same time would have uncertain physiological effect(s).

Diabetic dyslipidemia is characterized by multiple lipoprotein defects, including moderately high serum levels of cholesterol and triglycerides, small LDL particles, and low levels of HDL cholesterol. The results of recent clinical trials reveal beneficial effects of cholesterol-lowering therapy in diabetic and nondiabetic patients, thus supporting increased emphasis on treatment of diabetic dyslipidemia. This need for intensive treatment of diabetic dyslipidemia was advocated by the National Cholesterol Education Program's Adult Treatment Panel III.

Obesity is a well-known risk factor for the development of many very common diseases such as atherosclerosis, hypertension and diabetes. The incidence of obese people and thereby also these diseases is increasing throughout the entire industrialized world. Except for exercise, diet and food restriction no convincing pharmacological treatment for reducing body weight effectively and acceptably currently exist. However, due to its indirect but important effect as a risk factor in mortal and common diseases it will be important to find treatment for obesity or appetite regulation. Even mild obesity increases the risk for premature death, diabetes, hypertension, atherosclerosis, gallbladder disease and certain types of cancer. In the industrialized western world the prevalence of obesity has increased significantly in the past few decades. Because of the high prevalence of obesity and its health consequences, its prevention and treatment should be a high public health priority.

At present a variety of techniques are available to effect initial weight loss. Unfortunately, initial weight loss is not an optimal therapeutic goal. Rather, the problem is that most obese patients eventually regain their weight. An effective means to establish and/or sustain weight loss is the major challenge in the treatment of obesity today.

Accordingly, a need exists for compounds that are useful for inhibiting DPP-IV without suppressing the immune system.

Several compounds have been shown to inhibit DPP-IV, but all of these have limitations in relation to the potency, stability, selectivity, toxicity, and/or pharmacodynamic properties. Such compounds have been disclosed, for example, in WO 98/19998, WO 00/34241, U.S. Pat. No. 6,124,305 (Novartis AG), and WO 99/38501 (Trustees of Tufts University).

SUMMARY OF THE INVENTION

In accordance with one aspect of the present invention, there are provided compounds that are effective in treating conditions that may be regulated or normalized via inhibition of DPP-IV. More particularly, the invention relates to constrained cyano-containing bicyclic heterocycles and their derivatives that selectively inhibit DPP-IV, and to methods for making such compounds and intermediates useful therefore. In other aspects of the invention, there are provided pharmaceutical compositions comprising the compounds of the invention, and combinations thereof including one or more other types of antidiabetic agents; methods for inhibiting DPP-IV comprising administering to a patient in need of such treatment a therapeutically effective amount thereof; and compounds for use as a pharmaceutical, and their use in a process for the preparation of a medicament for treating conditions that are regulated or normalized via inhibition of DPP-IV.

DETAILED DESCRIPTION OF THE INVENTION

It has been discovered that constrained cyano compounds of the invention display marked selectivity for DPP-IV relative to related dipeptidyl peptidase enzymes. By selectivity for DPP-IV it is meant that the compounds more strongly inhibit DPP-IV than at least one closely related enzyme such as DPP-VII, DPP-VIII, DPP-IX and FAP. While not wishing to be bound by any theory, it is believed that this unexpected selectivity for DPP-IV results in an improved therapeutic profile with diminished side-effects compared to other non-selective DPP-IV inhibitors. In particular it is believed that potent inhibition of DPP-VIII by previous inhibitors correlates with the acute toxicity observed in animal studies. Inventive compounds avoid significant inhibition of DPP-VIII and therefore should avoid side-effects associated with DPP-VIII inhibition.

In addition to selectivity, constrained cyano compounds exhibit other advantages over previous inhibitors of DPP-IV. Compared to unconstrained inhibitors of DPP-IV, compounds of the present invention possess improved chemical stability and potentially fewer safety issues. For example, linear cyanopyrrolidides undergo irreversible cyclization to the inactive imidate and diketopiperazine compounds when dissolved (see Scheme 1). This results in an irreversible loss of activity since the cyclic forms of the linear compound do not inhibit DPP-IV. In addition, the multiple cyclic forms of the original linear compound may have different pharmacological profiles from the parent and may result in adverse safety consequences. At a minimum the multiple cyclic forms complicate clinical assessment of the cyanopyrrolidides.

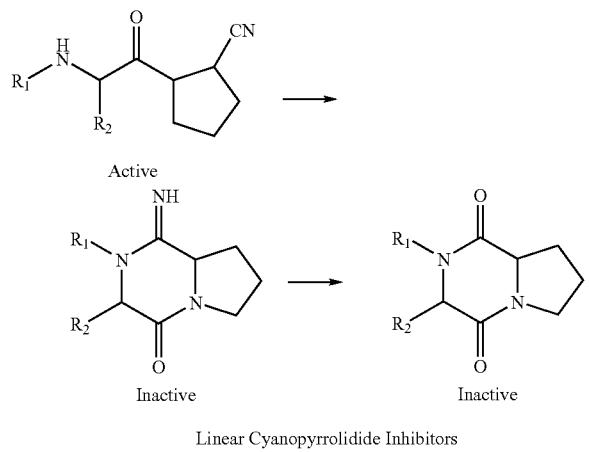

Linear Cyanopyrrolidide Inhibitors

In contrast, the DPP-IV inhibitors described herein do not undergo this cyclization as a result of the constrained nature of the bicyclic ring. Consequently the constrained cyano inhibitors do not exhibit this chemical loss of activity, and mitigate the potential safety issues from the formation of multiple structures derived from the parent inhibitor.

In accordance with one aspect, the present invention provides compounds of Formula I:

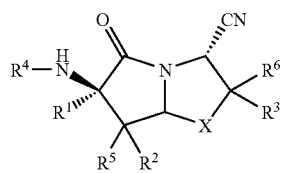

and stereoisomers, solvates, hydrates, tautomers, prodrugs, pharmaceutically acceptable salts, and mixtures thereof, wherein:

X is CRR', S, or O; or X is CR and forms a double bond with one of the carbons to which it is attached;

$R^1$ and $R^4$ are independently H or a substituted or unsubstituted alkyl, alkenyl, alkynyl, cycloalkyl, (cycloalkyl)alkyl, cycloalkenyl, (cycloalkenyl)alkyl, aryl, aralkyl, heterocyclyl, or heterocyclylalkyl, group, wherein the alkyl, alkenyl and alkynyl groups and the alkyl moieties of the (cycloalkyl)alkyl, (cycloalkenyl)alkyl, aralkyl, and heterocyclylalkyl groups optionally and independently comprise 1, 2, or 3 groups selected from O, NH, S, SO, $SO_2$, or a 3, 4, 5, or 6 member divalent carbocyclyl or heterocyclyl group;

R, R', $R^2$, $R^3$, $R^5$ and $R^6$ are independently H, F, Cl, Br, I, $OR^a$, $NR^aR^b$, CN, $NO_2$, $C(O)R^a$, $C(O)OR^b$, $C(O)NR^aR^b$, $NHC(O)R^a$, $NHC(O)OR^a$, or a substituted or unsubstituted alkyl, alkenyl, alkynyl, cycloalkyl, (cycloalkyl)alkyl, cycloalkenyl, (cycloalkenyl)alkyl, aryl, aralkyl, heterocyclyl, or heterocyclylalkyl, group, wherein the alkyl, alkenyl and alkynyl groups and the alkyl moieties of the (cycloalkyl)alkyl, (cycloalkenyl)alkyl, aralkyl, and heterocyclylalkyl groups optionally and independently comprise 1, 2, or 3 groups selected from O, NH, S, SO, $SO_2$, or a 3, 4, 5, or 6 member divalent carbocyclyl or heterocyclyl group; or $R^2$ and $R^5$ taken together are an oxo group, $R^3$ and $R^6$ taken together are an oxo group, or both $R^2$ and $R^5$ and $R^3$ and $R^6$ are oxo groups; and $R^a$ and $R^b$ at each occurrence are independently H or a substituted or unsubstituted alkyl, alkenyl, alkynyl, cycloalkyl, (cycloalkyl)alkyl, cycloalkenyl, (cycloalkenyl)alkyl, aryl, aralkyl, heterocyclyl, or heterocyclylalkyl group.

In some embodiments of compounds of Formula I, X is $CH_2$, S, or O. In others, X is S or O.

In some embodiments of compounds of Formula I, $R^1$ and $R^4$ are independently:

a) H;

b) $(C_{1-12})$alkyl, $(C_{2-12})$alkenyl, $(C_{2-12})$alkynyl, $(C_{3-12})$cycloalkyl, $(C_{3-12})$(cycloalkyl)alkyl, $(C_{3-12})$cycloalkenyl, or $(C_{3-12})$(cycloalkenyl)alkyl; wherein each group is optionally mono- or independently plurisubstituted with $R^7$, and wherein the alkyl, alkenyl, and alkynyl groups optionally and independently comprise 1, 2, or 3 groups selected from O, NH, S, SO, $SO_2$, or a 3, 4, 5, or 6 member divalent carbocyclyl or heterocyclyl group; wherein $R^7$ is halogen; $(C_{1-10})$alkyl; $(C_{1-10})$alkoxy; $(C_{3-10})$cycloalkyl; —$SR^8$; —$SOR^8$; —$SO_2R^8$; —$COR^8$; —$CO_2R^8$; —$CONHR^8$; —$CON(R^8)_2$—$OC(O)NHR^8$; —$OC(O)N(R^8)_2$, —$OR^8$; carboxy; cyano; nitro; oxo; hydroxyl; hydroxy$(C_{1-6})$alkyl; hydroxymethyl; N-hydroxyimino; trifluoromethyl; trifluoromethoxy; sulfamoyl; sulfonamido; carbamoyl; azido; amidino; guanidino; amino, wherein the amino group is optionally mono- or independently plurisubstituted with $R^8$, —$SOR^8$, —$SO_2R^8$, —$COR^8$, —$CO_2R^8$, —$CONHR^8$, —$CON(R^8)_2$, —$OR^8$, or —$SR^8$; aryl; heterocyclyl; or heteroaryl; wherein the aryl, heterocyclyl, and heteroaryl groups are optionally mono- or independently plurisubstituted with $R^9$;

each $R^8$ is independently $(C_{1-10})$alkyl; $(C_{2-10})$alkenyl; $(C_{2-10})$alkynyl; $(C_{3-10})$cycloalkyl; $(C_{5-10})$cycloalkenyl; benzyl; phenethyl; aryl; heterocyclyl; or heteroaryl; wherein the alkyl, alkenyl, alkynyl, cycloalkyl, and cycloalkenyl groups are optionally mono- or independently disubstituted with $R^{10}$; and wherein the aryl, heterocyclyl, and heteroaryl groups are optionally mono- or independently plurisubstituted with $R^{11}$;

$R^9$ is halogen; $(C_{1-10})$alkyl; $(C_{1-10})$alkoxy; $(C_{3-10})$cycloalkyl; —$SR^8$; —$SOR^8$; —$SO_2R^8$; —$COR^8$; —$CO_2R^8$; —$CONHR^8$; —$CON(R^8)_2$; —$OC(O)NHR^8$; —$OC(O)N(R^8)_2$, —$OR^8$; carboxy; cyano; nitro; oxo; hydroxyl; hydroxy$(C_{1-6})$alkyl; hydroxymethyl; N-hydroxyimino; trifluoromethyl; trifluoromethoxy; trifluoromethylthio, sulfamoyl; sulfonamido; carbamoyl; amidino; guanidino; phenyl, phenoxy, benzyl; benzyloxy; azido; amino, wherein the amino group is optionally mono- or independently plurisubstituted with $R^8$, —$SOR^8$, —$SO_2R^8$, —$COR^8$, —$CO_2R^8$, —$CONHR^8$, —$CON(R^8)_2$, —$OR^8$, or —$SR^8$; $(C_{1-10})$alkylamino; or $(C_{1-10})$dialkylamino;

$R^{10}$ is aryl, heterocyclyl, or heteroaryl, wherein each group is optionally mono- or independently plurisubstituted with $R^{11}$;

$R^{11}$ is halogen; $(C_{1-10})$alkyl; $(C_{1-10})$alkoxy; $(C_{1-10})$alkylamino; $(C_{1-10})$ dialkylamino; phenyl, phenoxy, benzyl; benzyloxy; hydroxyl$(C_{1-6})$alkyl; hydroxymethyl; nitro; trifluoromethyl; trifluoromethoxy; trifluoromethylthio; N-hydroxyimino; cyano; carboxy; acetamido; hydroxy; sulfonamido; or amino;

c) phenyl, phenyl fused to a $(C_{3-10})$cycloalkyl; monocyclic heteroaryl, or monocyclic heteroaryl fused to a $(C_{3-10})$ cycloalkyl; wherein the phenyl and heteroaryl groups are optionally mono- or independently plurisubstituted with $R^9$;

d) indanyl; 1,2,3,4-tetrahydronaphthyl; —$(CH_2)_j$-adamantyl in which j is 0, 1, 2, or 3; (4-pentylbicyclo[2.2.2]oct-1-yl)amine; or a [2.2.1] or [3.1.1] bicyclic carbocyclyl group, wherein the indanyl, 1,2,3,4-tetrahydronaphthyl, —$(CH_2)_j$-adamantyl, and [2.2.1] or [3.1.1] bicyclic carbocyclyl groups are optionally mono- or independently plurisubstituted with hydroxy, $(C_{1-8})$alkyl, $(C_{1-8})$alkoxy, $(C_{1-8})$alkanoyloxy, or $R^{12}R^{13}N$—CO—O—, wherein $R^{12}$ and $R^{13}$ are independently $(C_{1-8})$alkyl, or phenyl, wherein the alkyl and phenyl groups are optionally mono- or independently plurisubstituted with $(C_{1-8})$alkyl, $(C_{1-8})$alkoxy, halogen, or trifluoromethyl, or $R^{12}$ and $R^{13}$ together are $(C_{3-6})$alkylene;

e) $R^{14}(CH_2)_p$— wherein $R^{14}$ is pyrrolyl, pyrrolidinyl, 2-oxopyrrolidinyl, imidazolyl, pyrazolyl, thiophenyl, thiazolyl, furanyl, tetrahydrofuranyl, oxazolyl, oxazolidinyl, piperidinyl, piperazinyl, morpholinyl, pyridinyl, indolyl, isoindolyl, benzofuranyl, benzothiophenyl, purinyl, pyrimidinyl, quinolinyl, $(C_{1-6})$alkoxy, phenyl, phenoxy, $(C_{1-8})$cycloalkyl, naphthyl, cyclohexenyl, or adamantyl; each of which groups is optionally mono- or independently di- or trisubstituted with $R^{15}$; or $R^{14}$ is a [3.3.3] bicyclic carbocyclyl group, optionally mono- or independently plurisubstituted with $(C_{1-8})$alkyl; and p is 0, 1, 2, or 3; and wherein $R^{15}$ is halogen; cyano; nitro; $(C_{1-6})$alkyl; $(C_{1-6})$alkoxy; cycloalkyl; carboxy; $C(O)NHR^8$; hydroxy; hydroxy$(C_{1-6})$alkyl; hydroxymethyl; trifluoromethyl; trifluoromethoxy; sulfamoyl; carbamoyl; sulfonamido; aryl; heterocyclyl; or heteroaryl; wherein the aryl, heterocyclyl, and heteroaryl groups are optionally mono- or independently plurisubstituted with $R^9$; or f) $(R^{16})_2CH(CH_2)_q$—, wherein $R^{16}$ is phenyl; in which the phenyl groups are independently optionally mono- or independently disubstituted with $R^{15}$; and q is 0, 1, 2, or 3.

In some such embodiments, $R^1$ and $R^4$ are independently a) H;

b) $(C_{1-12})$alkyl, $(C_{2-12})$alkenyl, $(C_{2-12})$alkynyl, $(C_{3-12})$cycloalkyl, or $(C_{3-12})$cycloalkenyl; wherein each group is optionally mono- or independently plurisubstituted with $R^7$;

c) phenyl, phenyl fused to a $(C_{3-10})$cycloalkyl, monocyclic heteroaryl, or monocyclic heteroaryl fused to a $(C_{3-10})$ cycloalkyl; wherein the phenyl and heteroaryl groups are optionally mono- or independently plurisubstituted with $R^9$;

d) $R^{14}(CH_2)_p$—; or e) $(R^{16})_2CH(CH_2)_q$—.

In other embodiments of compounds of Formula I, $R^1$ is H or a methyl, ethyl, n-propyl, isopropyl, n-butyl, isobutyl, sec-butyl, cyclopentyl, cyclopentyl-$(CH_2)$—, cyclohexyl, cyclohexyl-$(CH_2)$—, phenyl, benzyl, phenylethyl, imidazolyl-$(CH_2)$—, or indolyl-$(CH_2)$— group, each of which is optionally substituted with 1 or 2 substituents that are each independently F, Cl, Br, I, hydroxy, oxo, cyano, amino, methylamino, dimethylamino, azido, nitro, $(C_{1-4})$alkoxy, trifluoromethyl, trifluoromethoxy, carboxyl, carboxamido, SH, $S(O)_{0-2}CH_3$, or guanidino. In certain embodiments, $R^1$ is not H.

In still other embodiments, $R^4$ is H. In some embodiments $R^4$ is not H.

In some embodiments of compounds of Formula I, one, two, or three of $R^2$, $R^3$, $R^5$, and $R^6$ are H. In others, $R^5$ is H, $R^6$ is H, or both $R^5$ and $R^6$ are H. In still others, $R^2$ and $R^3$ are independently selected from H, F, Cl, OH, or a substituted or unsubstituted $C_{1-6}$ alkyl, phenyl, or benzyl group. In certain embodiments, $R^5$ and $R^6$ are independently selected from H, F, Cl, or a substituted or unsubstituted $C_{1-6}$ alkyl, phenyl, or benzyl group. In yet others, each of $R^2$, $R^3$, $R^5$, and $R^6$ is H.

In another aspect the invention provides compounds of Formula II:

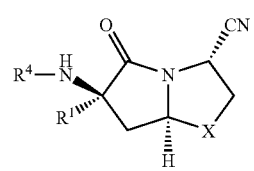

II and stereoisomers, solvates, hydrates, tautomers, pharmaceutically acceptable salts, and mixtures thereof, wherein:

X is $CH_2$, S, or O; or X is CH and forms a double bond with one of the carbons to which it is attached;

$R^1$ and $R^4$ are independently H or a substituted or unsubstituted alkyl, alkenyl, alkynyl, cycloalkyl, (cycloalkyl)alkyl, cycloalkenyl, (cycloalkenyl)alkyl, aryl, aralkyl, heterocyclyl, or heterocyclylalkyl, group, wherein the alkyl, alkenyl and alkynyl groups and the alkyl moieties of the (cycloalkyl)alkyl, (cycloalkenyl)alkyl, aralkyl, and heterocyclylalkyl groups optionally and independently comprise 1, 2, or 3 groups selected from O, NH, S, SO, $SO_2$, or a 3, 4, 5, or 6 member divalent carbocyclyl or heterocyclyl group.

In some embodiments of compounds of Formula II, X is O or S.

In some embodiments of compounds of Formula II, $R^1$ and $R^4$ are independently:
a) H;
b) $(C_{1-12})$alkyl, $(C_{2-12})$alkenyl, $(C_{2-12})$alkynyl, $(C_{3-12})$cycloalkyl, $(C_{3-12})$(cycloalkyl)alkyl, $(C_{3-12})$cycloalkenyl, or $(C_{3-12})$(cycloalkenyl)alkyl; wherein each group is optionally mono- or independently plurisubstituted with $R^7$, and wherein the alkyl, alkenyl, and alkynyl groups optionally and independently comprise 1, 2, or 3 groups selected from O, NH, S, SO, $SO_2$, or a 3, 4, 5, or 6 member divalent carbocyclyl or heterocyclyl group; wherein
  $R^7$ is halogen; $(C_{1-10})$alkyl; $(C_{1-10})$alkoxy; $(C_{3-10})$cycloalkyl; —$SR^8$; —$SOR^8$; —$SO_2R^8$; —$COR^8$; —$CO_2R^8$; —$CONHR^8$; —$CON(R^8)_2$; —OC(O)NHR^8$; —$OC(O)N(R^8)_2$, —$OR^8$; carboxy; cyano; nitro; oxo; hydroxyl; hydroxy$(C_{1-6}$alkyl; hydroxymethyl; N-hydroxyimino; trifluoromethyl; trifluoromethoxy; sulfamoyl; sulfonamido; carbamoyl; azido; amidino; guanidino; amino, wherein the amino group is optionally mono- or independently plurisubstituted with $R^8$, —$SOR^8$, —$SO_2R^8$, —$COR^8$, —$CO_2R^8$, —$CONHR^8$, —$CON(R^8)_2$, —$OR^8$, or —$SR^8$; aryl; heterocyclyl; or heteroaryl; wherein the aryl, heterocyclyl, and heteroaryl groups are optionally mono- or independently plurisubstituted with $R^9$;
  each $R^8$ is independently $(C_{1-10})$alkyl; $(C_{2-10})$alkenyl; $(C_{2-10})$alkynyl; $(C_{3-10})$cycloalkyl; $(C_{5-10})$cycloalkenyl; benzyl; phenethyl; aryl; heterocyclyl; or heteroaryl; wherein the alkyl, alkenyl, alkynyl, cycloalkyl, and cycloalkenyl groups are optionally mono- or independently disubstituted with $R^{10}$; and wherein the aryl, heterocyclyl, and heteroaryl groups are optionally mono- or independently plurisubstituted with $R^{11}$;
  $R^9$ is halogen; $(C_{1-10})$alkyl; $(C_{1-10})$alkoxy; $(C_{3-10})$cycloalkyl; —$SR^8$; —$SOR^8$; —$SO_2R^8$; —$COR^8$; —$CO_2R^8$; —$CONHR^8$; —$CON(R^8)_2$; —$OC(O)NHR^8$; —$OC(O)N(R^8)_2$, —$OR^8$; carboxy; cyano; nitro; oxo; hydroxyl; hydroxy$(C_{1-6}$alkyl; hydroxymethyl; N-hydroxyimino; trifluoromethyl; trifluoromethoxy; trifluoromethylthio, sulfamoyl; sulfonamido; carbamoyl; amidino; guanidino; phenyl, phenoxy, benzyl; benzyloxy; azido; amino, wherein the amino group is optionally mono- or independently plurisubstituted with $R^8$, —$SOR^8$, —$SO_2R^8$, —$COR^8$, —$CO_2R^8$, —$CONHR^8$, —$CON(R^8)_2$, —$OR^8$, or —$SR^8$; $(C_{1-10})$alkylamino; or $(C_{1-10})$dialkylamino;
  $R^{10}$ is aryl, heterocyclyl, or heteroaryl, wherein each group is optionally mono- or independently plurisubstituted with $R^{11}$;
  $R^{11}$ is halogen; $(C_{1-10})$alkyl; $(C_{1-10})$alkoxy; $(C_{1-10})$alkylamino; $(C_{1-10})$ dialkylamino; phenyl, phenoxy, benzyl; benzyloxy; hydroxyl$(C_{1-6})$alkyl; hydroxymethyl; nitro; trifluoromethyl; trifluoromethoxy; trifluoromethylthio; N-hydroxyimino; cyano; carboxy; acetamido; hydroxy; sulfonamido; or amino;
c) phenyl, phenyl fused to a $(C_{3-10})$cycloalkyl; monocyclic heteroaryl, or monocyclic heteroaryl fused to a $(C_{3-10})$cycloalkyl; wherein the phenyl and heteroaryl groups are optionally mono- or independently plurisubstituted with $R^9$;
d) indanyl; 1,2,3,4-tetrahydronaphthyl; —$(CH_2)_j$-adamantyl in which j is 0, 1, 2, or 3; (4-pentylbicyclo[2.2.2]oct-1-yl)amine; or a [2.2.1] or [3.1.1] bicyclic carbocyclyl group, wherein the indanyl, 1,2,3,4-tetrahydronaphthyl, —$(CH_2)_j$-adamantyl, and [2.2.1] or [3.1.1] bicyclic carbocyclyl groups are optionally mono- or independently plurisubstituted with hydroxy, $(C_{1-8})$alkyl, $(C_{1-8})$alkoxy, $(C_{1-8})$alkanoyloxy, or $R^{12}$ $R^{13}$N—CO—O—, wherein $R^{12}$ and $R^{13}$ are independently $(C_{1-8})$alkyl, or phenyl, wherein the alkyl and phenyl groups are optionally mono- or independently plurisubstituted with $(C_{1-8})$alkyl, $(C_{1-8})$alkoxy, halogen, or trifluoromethyl, or $R^{12}$ and $R^{13}$ together are $(C_{3-6})$alkylene;
e) $R^{14}(CH_2)_p$—wherein $R^{14}$ is pyrrolyl, pyrrolidinyl, 2-oxopyrrolidinyl, imidazolyl, pyrazolyl, thiophenyl, thiazolyl, furanyl, tetrahydrofuranyl, oxazolyl, oxazolidinyl, piperidinyl, piperazinyl, morpholinyl, pyridinyl, indolyl, isoindolyl, benzofuranyl, benzothiophenyl, purinyl, pyrimidinyl, quinolinyl, $(C_{1-6})$alkoxy, phenyl, phenoxy, $(C_{1-8})$cycloalkyl, naphthyl, cyclohexenyl, or adamantyl; each of which groups is optionally mono- or independently di- or trisubstituted with $R^{15}$; or $R^{14}$ is a [3.3.3] bicyclic carbocyclyl group, optionally mono- or independently plurisubstituted with $(C_{1-8})$alkyl; and p is 0, 1, 2, or 3; and wherein
  $R^{15}$ is halogen; cyano; nitro; $(C_{1-6})$alkyl; $(C_{1-6})$alkoxy; cycloalkyl; carboxy; C(O)NHR^8$; hydroxy; hydroxy $(C_{1-6})$alkyl; hydroxymethyl; trifluoromethyl; trifluoromethoxy; sulfamoyl; carbamoyl; sulfonamido; aryl; heterocyclyl; or heteroaryl; wherein the aryl, heterocyclyl, and heteroaryl groups are optionally mono- or independently plurisubstituted with $R^9$; or
f) $(R^{16})_2CH(CH_2)_q$—, wherein $R^{16}$ is phenyl; in which the phenyl groups are independently optionally mono- or independently disubstituted with $R^{15}$; and q is 0, 1, 2, or 3.

In other embodiments of compounds of formula II, $R^1$ and $R^4$ are independently
a) H;
b) $(C_{1-12})$alkyl, $(C_{2-12})$alkenyl, $(C_{2-12})$alkynyl, $(C_{3-12})$cycloalkyl, or $(C_{3-12})$cycloalkenyl; wherein each group is optionally mono- or independently plurisubstituted with $R^7$;
c) phenyl, phenyl fused to a $(C_{3-10})$cycloalkyl, monocyclic heteroaryl, or monocyclic heteroaryl fused to a $(C_{3-10})$cycloalkyl; wherein the phenyl and heteroaryl groups are optionally mono- or independently plurisubstituted with $R^9$;
d) $R^{14}(CH_2)_p$—; or
e) $(R^{16})_2CH(CH_2)_q$—.

In still other embodiments of compounds of Formula II, $R^1$ is H or a methyl, ethyl, n-propyl, isopropyl, n-butyl, isobutyl, sec-butyl, cyclopentyl, cyclopentyl-$(CH_2)$—, cyclohexyl, cyclohexyl-$(CH_2)$—, phenyl, benzyl, phenylethyl, imidazolyl-$(CH_2)$—, or indolyl-$(CH_2)$— group, each of which is optionally substituted with 1 or 2 substituents that are each independently F, Cl, Br, I, hydroxy, oxo, cyano, amino, methylamino, dimethylamino, azido, nitro, $(C_{1-4})$alkoxy, trifluoromethyl, trifluoromethoxy, carboxyl, carboxamido, SH, $S(O)_{0-2}CH_3$, or guanidino. In yet other embodiments, $R^4$ is H.

Compounds of the invention include mixtures of stereoisomers such as mixtures of diastereomers and/or enantiomers. In some embodiments, the compound, e.g. of Formula I or II, is 90 weight percent (wt %) or greater of a single diastereomer of enantiomer. In other embodiments, the compound is 92, 94, 96, 98 or even 99 wt % or more of a single diastereomer or single enantiomer.

In another aspect, compounds of the invention further include an 8-member bicyclic heterocycle comprising a pyrrolidinonyl ring, wherein the heterocycle is substituted with a cyano group and a basic group having a pKa of about 6 to about 10, and wherein the heterocycle inhibits DPP-IV with a Ki of 10 uM or less. Exemplary basic groups include aminoalkyl and amino groups. In some embodiments, the bicyclic heterocycle is a compound of Formula III:

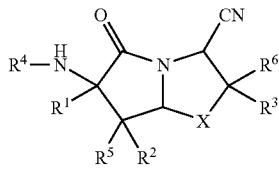

III and stereoisomers, solvates, hydrates, tautomers, prodrugs, pharmaceutically acceptable salts, and mixtures thereof, wherein:

X is CRR', S, or O; or X is CR and forms a double bond with one of the carbons to which it is attached;

$R^1$ and $R^4$ are independently H or a substituted or unsubstituted alkyl, alkenyl, alkynyl, cycloalkyl, (cycloalkyl)alkyl, cycloalkenyl, (cycloalkenyl)alkyl, aryl, aralkyl, heterocyclyl, or heterocyclylalkyl, group, wherein the alkyl, alkenyl and alkynyl groups and the alkyl moieties of the (cycloalkyl)alkyl, (cycloalkenyl)alkyl, aralkyl, and heterocyclylalkyl groups optionally and independently comprise 1, 2, or 3 groups selected from O, NH, S, SO, $SO_2$, or a 3, 4, 5, or 6 member divalent carbocyclyl or heterocyclyl group;

R, R', $R^2$, $R^3$, $R^5$ and $R^6$ are independently H, F, Cl, Br, I, $OR^a$, $NR^aR^b$, CN, $NO_2$, $C(O)R^a$, $C(O)OR^b$, $C(O)NR^aR^b$, $NHC(O)R^a$, $NHC(O)OR^a$, or a substituted or unsubstituted alkyl, alkenyl, alkynyl, cycloalkyl, (cycloalkyl)alkyl, cycloalkenyl, (cycloalkenyl)alkyl, aryl, aralkyl, heterocyclyl, or heterocyclylalkyl, group, wherein the alkyl, alkenyl and alkynyl groups and the alkyl moieties of the (cycloalkyl)alkyl, (cycloalkenyl)alkyl, aralkyl, and heterocyclylalkyl groups optionally and independently comprise 1, 2, or 3 groups selected from O, NH, S, SO, $SO_2$, or a 3, 4, 5, or 6 member divalent carbocyclyl or heterocyclyl group; or $R^2$ and $R^5$ taken together are an oxo group, $R^3$ and $R^6$ taken together are an oxo group, or both $R^2$ and $R^5$ and $R^3$ and $R^6$ are oxo groups; and $R^a$ and $R^b$ at each occurrence are independently H or a substituted or unsubstituted alkyl, alkenyl, alkynyl, cycloalkyl, (cycloalkyl)alkyl, cycloalkenyl, (cycloalkenyl)alkyl, aryl, aralkyl, heterocyclyl, or heterocyclylalkyl group.

In some such embodiments of compounds of Formula III, each of $R^2$, $R^3$, $R^5$, and $R^6$ is H.

As set forth herein, compounds of the invention include both the neutral form of the compounds and pharmaceutically acceptable salts of the compounds, such as hydrochloride salts and other salts. Representative compounds of the invention thus include, but are not limited to:

6-Amino-5-oxo-hexahydro-pyrrolo[2,1-b]thiazole-3-carbonitrile hydrochloride,

6-Amino-6-methyl-5-oxo-hexahydro-pyrrolo[2,1-b]thiazole-3-carbonitrile,

6-Amino-6-ethyl-5-oxo-hexahydro-pyrrolo[2,1-b]thiazole-3-carbonitrile hydrochloride, 6-Amino-6-isopropyl-5-oxo-hexahydro-pyrrolo[2,1-b]thiazole-3-carbonitrile hydrochloride, 6-Amino-6-cyclopentyl-5-oxo-hexahydro-pyrrolo[2,1-b]thiazole-3-carbonitrile hydrochloride, 6-Amino-6-cyclohexyl-5-oxo-hexahydro-pyrrolo[2,1-b]thiazole-3-carbonitrile hydrochloride, 6-Amino-6-isobutyl-5-oxo-hexahydro-pyrrolo[2,1-b]thiazole-3-carbonitrile hydrochloride, 6-Amino-6-sec-butyl-5-oxo-hexahydro-pyrrolo[2,1-b]thiazole-3-carbonitrile hydrochloride, 6-Amino-5-oxo-6-phenethyl-hexahydro-pyrrolo[2,1-b]thiazole-3-carbonitrile hydrochloride, 6-Amino-6-benzyl-5-oxo-hexahydro-pyrrolo[2,1-b]thiazole-3-carbonitrile hydrochloride, 6-Amino-6-cyclohexylmethyl-5-oxo-hexahydro-pyrrolo[2,1-b]thiazole-3-carbonitrile hydrochloride, 6-Amino-6-(4-fluoro-phenyl)-5-oxo-hexahydro-pyrrolo[2,1-b]thiazole-3-carbonitrile hydrochloride, and 6-Amino-5-oxo-6-phenyl-hexahydro-pyrrolo[2,1-b]thiazole-3-carbonitrile hydrochloride.

In accordance with another aspect of the invention, there are provided intermediates for the synthesis of compounds of the invention. Such intermediates include compounds of Formula IV:

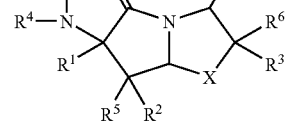

IV and stereoisomers, solvates, hydrates, tautomers, prodrugs, pharmaceutically acceptable salts, and mixtures thereof, wherein:

X is CRR', S, or O; or X is CR and forms a double bond with one of the carbons to which it is attached;

$R^1$ is H or a substituted or unsubstituted alkyl, alkenyl, alkynyl, cycloalkyl, (cycloalkyl)alkyl, cycloalkenyl, (cycloalkenyl)alkyl, aryl, aralkyl, heterocyclyl, or heterocyclylalkyl, group, wherein the alkyl, alkenyl and alkynyl groups and the alkyl moieties of the (cycloalkyl)alkyl, (cycloalkenyl)alkyl, aralkyl, and heterocyclylalkyl groups optionally and independently comprise 1, 2, or 3 groups selected from O, NH, S, SO, $SO_2$, or a 3, 4, 5, or 6 member divalent carbocyclyl or heterocyclyl group;

R, R', $R^2$, $R^3$, $R^5$ and $R^6$ are independently H, F, Cl, Br, I, $OR^a$, $NR^aR^b$, CN, $NO_2$, $C(O)R^a$, $C(O)OR^b$, $C(O)NR^aR^b$, $NHC(O)R^a$, $NHC(O)OR^a$, or a substituted or unsubstituted alkyl, alkenyl, alkynyl, cycloalkyl, (cycloalkyl)alkyl, cycloalkenyl, (cycloalkenyl)alkyl, aryl, aralkyl, heterocyclyl, or heterocyclylalkyl, group, wherein the alkyl, alkenyl and alkynyl groups and the alkyl moieties of the (cycloalkyl)alkyl, (cycloalkenyl)alkyl, aralkyl, and heterocyclylalkyl groups optionally and independently comprise 1, 2, or 3 groups selected from O, NH, S, SO, $SO_2$, or a 3, 4, 5, or 6 member divalent carbocyclyl or heterocyclyl group; or $R^2$ and $R^5$ taken together are an oxo group, $R^3$ and $R^6$ taken together are an oxo group, or both $R^2$ and $R^5$ and $R^3$ and $R^6$ are oxo groups;

$R^a$ and $R^b$ at each occurrence are independently H or a substituted or unsubstituted alkyl, alkenyl, alkynyl, cycloalkyl, (cycloalkyl)alkyl, cycloalkenyl, (cycloalkenyl)alkyl, aryl, aralkyl, heterocyclyl, or heterocyclylalkyl group;

$R^4$ is H, an amino protecting group, or a substituted or unsubstituted alkyl, alkenyl, alkynyl, cycloalkyl, (cycloalkyl)alkyl, cycloalkenyl, (cycloalkenyl)alkyl, aryl, aralkyl, heterocyclyl, or heterocyclylalkyl, group, wherein the alkyl, alkenyl and alkynyl groups and the alkyl moieties of the (cycloalkyl)alkyl, (cycloalkenyl) alkyl, aralkyl, and heterocyclylalkyl groups optionally and independently comprise 1, 2, or 3 groups selected from O, NH, S, SO, $SO_2$, or a 3, 4, 5, or 6 member divalent carbocyclyl or heterocyclyl group; and $R^{4a}$ is an amino protecting group; or $R^{4a}$ and $R^4$ together form a cyclic amino protecting group.

In some embodiments of compounds of Formula IV, $R^4$ is H and $R^{4a}$ is an amino protecting group. In other embodiments, the compounds have the Formula IVA:

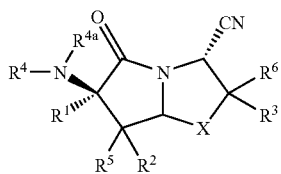

IVA

In some such embodiments, X is S. In others, each of $R^2$, $R^3$, $R^5$, and $R^6$ is H.

In other embodiments of compounds of Formula IV, the compounds have the Formula IVB:

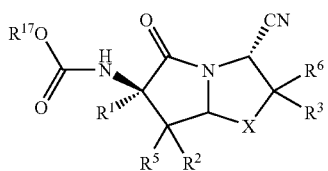

IVB wherein $R^{17}$ is a substituted or unsubstituted ($C_{1-6}$)alkyl or ($C_{6-20}$)aralkyl group. Typically, $R^{17}$ is an unsubstituted t-butyl, benzyl, or fluoren-9-ylmethyl group. Compound IV may occur as a single stereoisomer or as mixtures of stereoisomers that may be separated into the desired stereoisomer(s) according to well know techniques.

Scheme 2

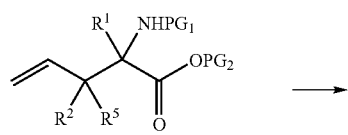

PG = protecting group

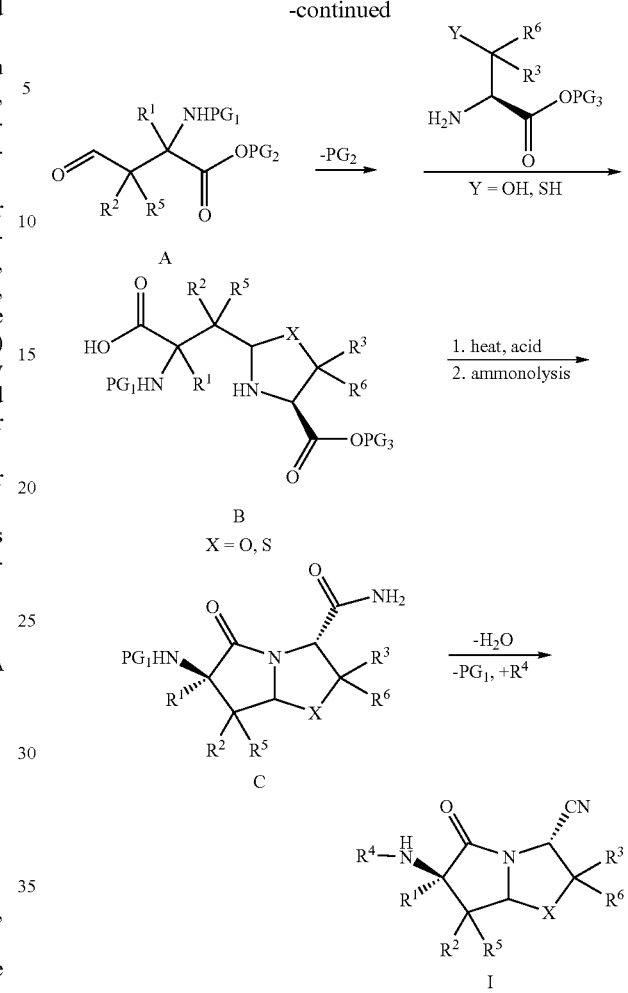

In yet another aspect of the invention, there are provided methods of making compounds of the invention, including but not limited to compounds of Formulas I, II, III, and IV. Compounds of the invention may be prepared by several routes, including, e.g., Allen, N. E., et al., *Tetrahedron* (1989) 45, 1905-28; Baldwin, J. E., et al., loc. cit. at 4537-50; and Khalil, E. M., et al., *J. Med. Chem.* (1999) 42, 2977. Scheme 2 illustrates the synthesis of compounds of Formula I from suitably protected alpha-allylated amino acids. The starting compounds may be prepared by methods known in the art such as allylation of an imine derivative of the amino acid to provide compound A. The olefinic group of A is oxidatively cleaved by, e.g., ozonolysis or another suitable method. Removal of the carboxyl protecting group $PG_2$, typically an ester, is followed by reaction with a suitably protected derivative of cysteine or serine to provide compound B. Formation of the bicyclic compound may then be effected by heating B in the presence of an acid catalyst. Ammonolysis to C (a compound of Formula IVA) and dehydration (e.g. trifluoroacetic anhydride or methyl N-(triethylammoniosulfonyl)carbamate (Burgess' reagent)) provide compounds of Formula I. The use of, e.g., L-Cys-OMe or L-Ser-OMe lead to compounds of Formula II. Non-hydrogen $R^4$ groups may be subsequently added by, e.g. reductive amination (such as with $NaCNBH_4$, NaOAc, methanol, molecular sieves), or may be installed prior to the dehydration step.

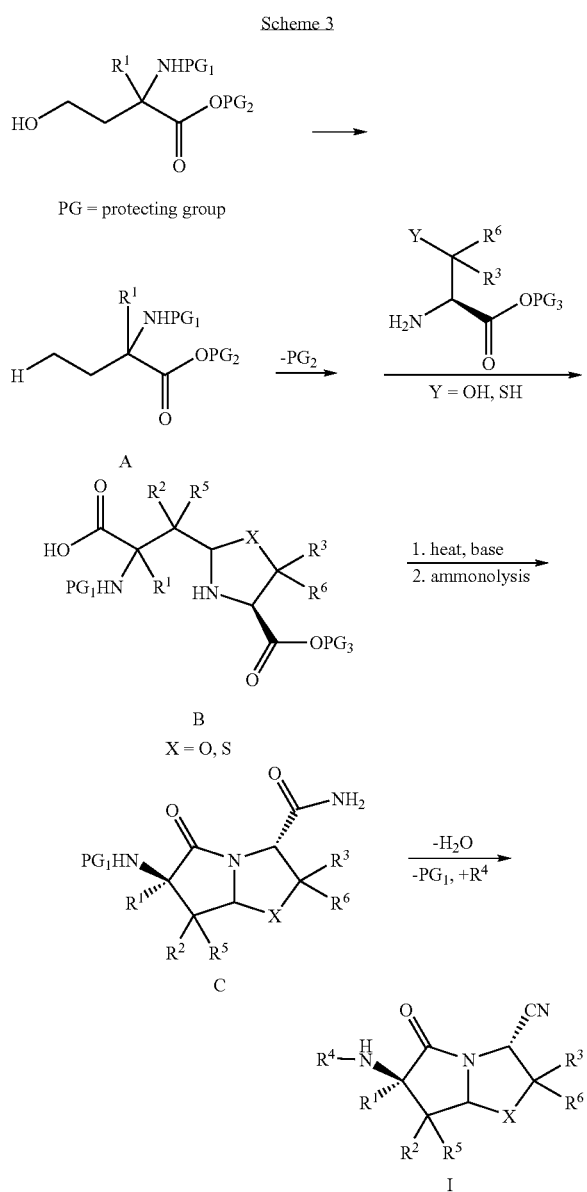

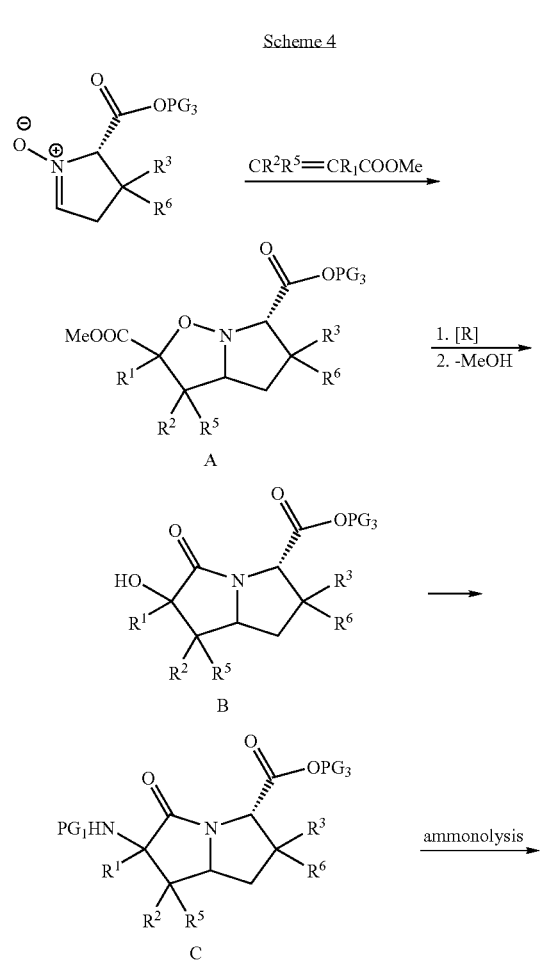

cysteine or serine residue to provide compound B. The pyrrolidinone ring of the bicyclic compound can be formed by either heating with base (e.g. pyridine and 4-dimethylaminopyridine) or another suitable reagent (2-chloro-N-methylpyridinium iodide). Ammonolysis to C and dehydration as above provide compounds of Formula I. As above, the use of, e.g., L-Cys-OMe or L-Ser-OMe lead to compounds of Formula II. Non-hydrogen $R^4$ groups may be subsequently added by, e.g. reductive amination, also as above, or may be installed prior to the dehydration step.

Compounds of the invention may be synthesized with the desired stereochemistry at various positions by using amino acid derivatives of the appropriate stereochemistry. For example, as shown in Schemes 2 and 3, use of L-cysteine methyl ester and its derivatives in the conversion of compound A to B results in a compound of Formula I where X is S and the carbon at the 3-position (i.e., alpha to the nitrile) has the L-configuration. Use of D-cysteine, D-serine or mixtures of D- and L-cysteine or serine or derivatives thereof provide compounds of Formula III. Alpha-substituted amino acids may be prepared in non-racemic form either by stereoselective synthesis or by enantiomeric and/or diastereomeric resolution techniques well know to those of skill in the art.

As shown in Scheme 3 and as described in the Examples, the compounds of Formula I may also be prepared by synthesis of suitably protected derivatives of aspartic acid. The latter compounds are well known in the art (see, e.g., Gerona-Navarro G; Bonache M A; Herranz R; Garcia-Lopez M T; Bonzalez-Muniz R, *J. Org. Chem.* 2001, 66, 3538-3547. Gerona-Navarro G; Garcia-Lopez M T; Gonzalez-Muniz R, *J. Org. Chem.* 2002 67, 3953-3956. Gerona-Novarro G; Garcia-Lopez M T; Gonzalez-Muniz R, *Tetrahedron Lett.* 2003, 44, 6145-6148. Dolbeare K; Pontoriero G F; Gupta S K; Mishra R K; Johnson R L, *J. Med. Chem.* 2003, 46, 727-733). The gamma carboxylate is converted to an aldehyde by, e.g., a two-step reduction/oxidation process (e.g., (1) $NaBH_4$ reduction of a mixed anhydride to the alcohol; (2) oxidation with pyridinium chlorochromate or other suitable reagent) to provide compound A. Compound A may be directly or indirectly (after removal of $PG_2$) reacted with a suitably protected

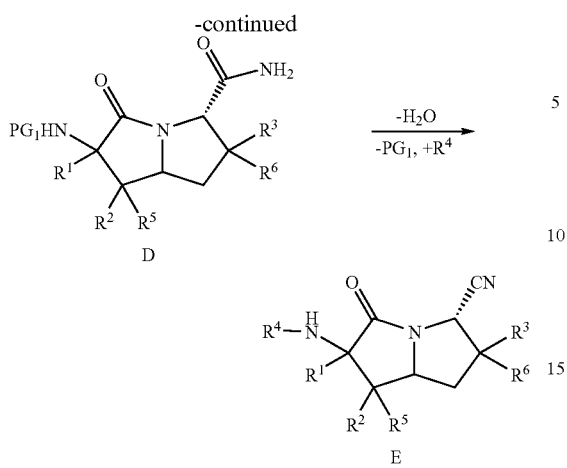

D

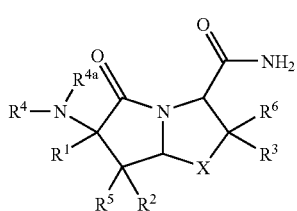

E

Compounds of the invention that have a carbone group as X (i.e., CRR') may be prepared as shown in Scheme 4 by modification of known methods (e.g., Baldwin et al., *Tetrahedron* (1984) 40, 4513). A cycloaddition of a suitably substituted acrylate ester (typically a methyl ester) with the pyrroline oxide as shown provides the bicyclic intermediate A Fission of the N—O bond by, e.g., hydrogenolysis (hydrogen, Raney Ni), affords the pyrrolidine which can be cyclized to the desired bicyclic compound B. The hydroxy of B may be converted to an N-protected amine by activation (e.g. by tosylation), displacement by azide, reduction (e.g., hydrogenolysis over Pd/C) and protection with any suitable group (e.g., Boc) to give compound C. Ammonolysis to D and dehydration as above provides compound E.

Thus, the methods of preparing compounds of the invention, e.g., Formula III, include exposing a compound of Formula V, stereoisomers, solvates, hydrates, tautomers, prodrugs, pharmaceutically acceptable salts, or mixtures thereof,

V

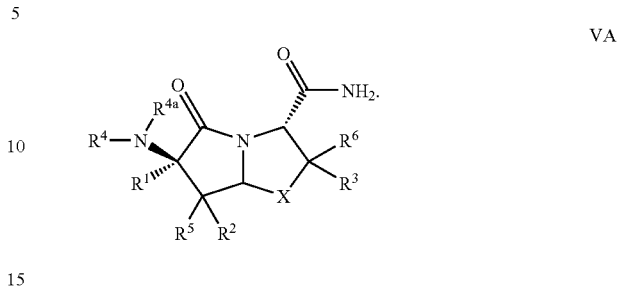

to a dehydrating agent to provide a compound of Formula IV, wherein X, $R^1$, $R^2$, $R^3$, $R^4$, $R^{4a}$, $R^5$, and $R^6$ are as defined for Formula IV. Suitable dehydrating agents include trifluoroacetic anhydride (TFAA), Burgess' reagent, and the like.

The methods of preparing compounds of the invention further include converting the compound of Formula IV to a compound of Formula III, as defined above. The methods include removing the amino protecting group(s) according to procedures known to those of skill in the art. Thus, in some such embodiments, $R^4$ is H and $R^{4a}$ is an amino-protecting group such as, but not limited to, Boc, Cbz, or Fmoc. In others, $R^4$ and $R^{4a}$ are both amino protecting groups and may be the same or different. In still other embodiments, $R^4$ and $R^{4a}$ together form a cyclic amino protecting group, e.g., phthalimide.

In some embodiments of methods of preparing compounds of the invention, the compound of Formula V has the structure of Formula VA:

VA

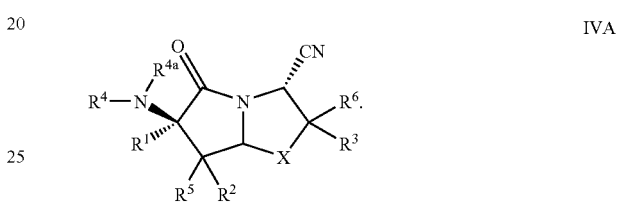

and the compound of Formula IV has the structure of Formula IVA:

IVA

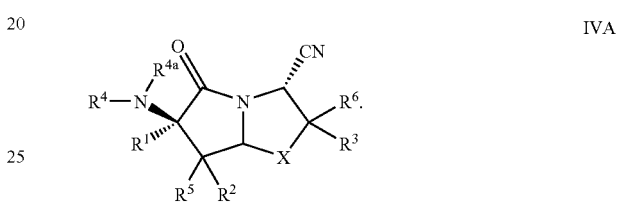

As above, the methods further include converting the compound of Formula IVA to Formula I as defined herein by removing the amino protecting group(s).

Methods/Uses

Another aspect of the invention provides methods and uses for constrained cyano compounds which are selective inhibitors of DPP-IV. For example, there are provided methods of inhibiting dipeptidyl peptidase-IV comprising contacting dipeptidyl peptidase-IV with a compound as described herein (e.g., a compound of Formula I, II, or III). Methods of inhibiting dipeptidyl peptidase-IV (DPP-IV) include methods for selectively inhibiting DPP-IV over related enzymes. By "selectively inhibiting DPP-IV" it is meant that a compound displays more potent inhibition of DPP-IV, as judged by Ki for example, compared to another enzyme. For example, in some embodiments of methods of inhibiting DPP-IV, DPP-IV is inhibited by greater than 5-fold relative to one or more other dipeptidyl peptidases. In other embodiments, DPP-IV is inhibited by 10-, 12-, 15-, 20-, 25-, 50- or even 100-fold or more over other dipeptidyl peptidases. In particular, the compound of Formula I or II can selectively inhibit DPP-IV over dipeptidyl peptidase-VII, or over dipeptidyl peptidase-VIII, or over dipeptidyl peptidase-IX, or over fibroblast activation protein (FAP). In some embodiments, the compounds of Formula I or II selectively inhibit DPP-IV over two or more of DPP-VII, DPP-VIII, DPP-IX, and FAP. For example, the compounds of Formula I or II can selectively inhibit DPP-VII and DPP-VIII, or DPP-VIII and FAP, or DPP-VII, DPP-VIII, and FAP. In still other embodiments, the compounds of Formula I selectively inhibit DPP-IV over DPP-VII, DPP-VIII, DPP-IX and FAP, or any combination thereof.

As selective inhibitors of DPP-IV, compounds of the invention are particularly well-suited for use in the treatment of DPP-IV mediated disorders and conditions. Thus, there are further provided methods for treating, controlling or preventing a DPP-IV mediated disorder or condition comprising administering to a mammal in need thereof an effective amount of a compound of the invention, including, but not limited to compounds of Formula I, II, or III. In some embodiments, the compound is a compound of Formula I and is 90 wt % or more of a single diastereomer. In some embodiments, the compound inhibits DPP-IV by 5-fold or more relative to at least one other dipeptidyl peptidase enzyme. In other embodiments, DPP-IV is inhibited by 10-, 12-, 15-, 20-, 25-, 50- or even 100-fold or more over other dipeptidyl peptidases. Exemplary other dipeptidyl peptidases include DPP-VII, DPP-VIII, DPP-IX, and FAP.

More specifically, DPP-IV mediated conditions include one or more of (1) hyperglycemia, (2) low glucose tolerance, (3) insulin resistance, (4) obesity, (5) lipid disorders, (6) atherosclerosis and its sequelae, (7) vascular restenosis, (8) irritable bowel syndrome, (9) inflammatory conditions, (10) growth hormone deficiency, (11) HIV infection, (12) pancreatitis, (13) abdominal obesity, (14) neurodegenerative disease, (15) multiple sclerosis, (16) retinopathy, (17) nephropathy, (18) neuropathy, (19) Syndrome X, (20) ovarian hyperandrogenism, (21) allograft rejection in transplantation, (22) diabetes, (23) neutropenia, (24) anemia, (25) neuronal disorders, (26) tumor growth and metastasis, (27) benign prostatic hypertrophy, (28) gingivitis, (29) hypertension, (30) osteoporosis, (31) dysmetabolic syndrome, (32) diabetic complications, (33) impaired glucose homeostasis, (34) infertility, (35) polycystic ovary syndrome, (36) growth disorders, (37) frailty, (38) autoimmune diseases, (39) intestinal diseases, and (40) anorexia nervosa.

In some embodiments, the DPP-IV condition is related to glucose metabolism. For example, the condition can be diabetes such as non-insulin dependent (Type 2) diabetes mellitus or insulin dependent (Type 1) diabetes mellitus. The condition can also be hyperglycemia or insulin resistance. Alternatively, insulin resistance is a component of another DPP-IV mediated condition. The condition may also be obesity. In some embodiments, the condition is a lipid disorder such as dyslipidemia, hyperlipidemia, hypertriglyceridemia, hypercholesterolemia, low HDL, or high LDL. In yet other embodiments, islet neogenesis, β-cell survival, or insulin biosynthesis is enhanced.

In other embodiments, the DPP-IV mediated condition is an inflammatory condition such as inflammatory bowel disease, Crohn's disease, ulcerative colitis, or rheumatoid arthritis.

Methods of treating, controlling, or preventing DPP-IV mediated conditions further include administering one or more other suitable compounds selected from the group consisting of:

a) Other dipeptidyl peptidase-IV inhibitors;
b) Insulin sensitizers selected from the group consisting of PPAR agonists, biguanides, and protein phosphatase-1 B inhibitors;
c) Insulin or insulin mimetics;
d) Sulfonylureas or other insulin secretagogues;
e) α-glucosidase inhibitors;
f) glucagons receptor agonists;
g) GLP-1, GLP-1 mimetics, and GLP-1 receptor agonists;
h) GLP-2, GLP-2 mimetics, and GLP-2 receptor agonists;
i) GIP, GIP mimetics, and GIP receptor agonists;
j) PACAP, PACAP mimetics, and PACAP receptor 3 agonists;
k) Cholesterol lowering agents selected from the group consisting of HMG-CoA reductase inhibitors, sequestrants, nicotinyl alcohol, nicotinic acid or a salt thereof, PPARα agonists, PPARα/γ dual agonists, inhibitors of cholesterol absorption, acyl CoA:cholesterol acyltransferase inhibitors, and anti-oxidants;
l) PPARδ agonists;
m) Anti-obesity compounds;
n) An ileal bile acid transporter inhibitor;
o) Anti-inflammatory agents;
p) G-CSF, G-CSF mimetics, and G-CSF receptor agonists; and
q) EPO, EPO mimetics, and EPO receptor agonists.

For example, where the one or more DPP-IV mediated conditions are selected from the group consisting of hypercholesterolemia, atherosclerosis, low HDL levels, high LDL levels, hyperlipidemia, hypertriglyceridemia, and dyslipidemia, the method can further include administering to a mammal in need of such treatment a therapeutically effective amount of an HMG-CoA reductase inhibitor. The HMG-CoA reductase inhibitor can be a statin such as lovastatin, simvastatin, pravastatin, fluvastatin, atorvastatin, itavastatin, ZD-4522 or rivastatin. In some embodiments, the condition is atherosclerosis and the HMC-CoA reductase inhibitor is a statin such as those listed above.

Where the DPP-IV mediated condition is related to glucose metabolism such as diabetes (including Type 1 and Type 2) hyperglycemia or insulin resistance, the method can further include administering to a mammal in need of such treatment a therapeutically effective amount of other dipeptidyl peptidase-IV inhibitors; insulin sensitizers; insulin or insulin mimetics; sulfonylureas or other insulin secretagogues; α-glucosidase inhibitors; glucagons receptor agonists; GLP-1, GLP-1 mimetics, and GLP-1 receptor agonists; GLP-2, GLP-2 mimetics, and GLP-2 receptor agonists; GIP, GIP mimetics, and GIP receptor agonists; PACAP, PACAP mimetics, and PACAP receptor 3 agonists; PPARδ agonists; anti-obesity compounds; or an ileal bile acid transporter inhibitor.

Where the DPP-IV mediated condition is obesity, the methods can further include administering to a mammal in need of such treatment a therapeutically effective amount of an anti-obesity agent. Suitable anti-obesity agents include a beta-3 adrenergic agonist, a CB1 cannabinoid antagonist, a lipase inhibitor, a serotonin and dopamine reuptake inhibitor, a thyroid receptor beta compound, an anorectic agent, a fatty acid oxidation upregulator, or a mixture of any two or more thereof. For example, the anti-obesity agent can be orlistat, ATL-962, AJ9677, L750355, CP331648, sibutramine, topiramate, axokine, dexamphetamine, phentermine, phenylpropanolamine, famoxin, mazindol, or a mixture of any two or more thereof.

Where the DPP-IV mediated condition is neutropenia, the methods can further include administering to a mammal in need of such treatment a therapeutically effective amount of a neutrophilic agent. Suitable neutrophilic agents include G-CSF, a G-CSF mimetic, a G-CSF receptor agonist or a mixture of any two or more thereof. For example, the neutrophilic agent can be pegfilgrastim, filgrastim, lenograstim, nartograstim, or a mixture of any two or more thereof.

Where the DPP-IV mediated condition is anemia, and further comprising administering to a mammal in need of such treatment a therapeutically effective amount of a erythropoietin agonist. Suitable erythropoietin agonists include EPO, an EPO mimetic, an EPO receptor agonist, or a mixture of any two or more thereof. For example, the erythropoietin agonist can be epoetin alfa, darbepoetin alfa, or a mixture of any two or more thereof. EPO mimetics include proteins and other comouns which mimic the biological effects of naturally occurring EPO.

A variety of uses of the invention compounds are possible along the lines of the various methods of the treating an individual such as a mammal described above. Exemplary uses of the invention methods are represented by:

Use of a compound of the invention for the manufacture of a medicament for treating a condition that may be regulated or normalized via inhibition of DPP-IV;

Use of a compound of the invention for the manufacture of a medicament for treatment of metabolic disorders;

Use of a compound of the invention for the manufacture of a medicament for blood glucose lowering;

Use of a compound of the invention for the manufacture of a medicament for treatment of type II diabetes;

Use of a compound of the invention for the manufacture of a medicament for the treatment of impaired glucose tolerance (IGT);

Use of a compound of the invention for the manufacture of a medicament for the treatment of impaired fasting glucose (IFG);

Use of a compound of the invention for the manufacture of a medicament for prevention of hyperglycemia;

Use of a compound of the invention for the manufacture of a medicament for delaying the progression of impaired glucose tolerance (IGT) to type II diabetes;

Use of a compound of the invention for the manufacture of a medicament for delaying the progression of non-insulin requiring type II diabetes to insulin requiring type II diabetes;

Use of a compound of the invention for the manufacture of a medicament for increasing the number and/or the size of beta cells in a mammalian subject;

Use of a compound of the invention for the manufacture of a medicament for treatment of beta cell degeneration, in particular apoptosis of beta cells;

Use of a compound of the invention for the manufacture of a medicament for the treatment of disorders of food intake;

Use of a compound of the invention for the manufacture of a medicament for the treatment of obesity;

Use of a compound of the invention for the manufacture of a medicament for appetite regulation or induction of satiety;

Use of a compound of the invention for the manufacture of a medicament for the treatment of dyslipidemia;

Use of a compound of the invention for the manufacture of a medicament for treatment of functional dyspepsia, in particular irritable bowel syndrome; and Methods for treating the conditions mentioned above by administering to a subject in need thereof an effective amount of a compound of the invention.

Pharmaceutical Compositions and Combination Treatments

A. Compositions. Another aspect of the invention provides pharmaceutical compositions of the compounds of the invention, alone or in combination with another type of antidiabetic agent and/or other type therapeutic agent. Pharmaceutical compositions containing a compound of the invention of the invention may be prepared by conventional techniques, e.g. as described in Remington: The Science and Practise of Pharmacy, 19th Ed., 1995. The compositions may appear in conventional forms, for example capsules, tablets, aerosols, solutions, suspensions or topical applications.

Typical compositions include a compound of the invention which inhibits the enzymatic activity of DPP-IV, and a pharmaceutically acceptable excipient which may be a carrier or a diluent. Compounds of the invention include, but are not limited to compounds of Formula I, II, or III. As set forth herein, compounds of the invention include stereoisomers, tautomers, solvates, prodrugs, pharmaceutically acceptable salts and mixtures thereof. The compound may be diluted by a carrier, or enclosed within a carrier which can be in the form of a capsule, sachet, paper or other container. In making the compositions, conventional techniques for the preparation of pharmaceutical compositions may be used.

For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material that acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax.

The formulations can be mixed with auxiliary agents which do not deleteriously react with the active compounds. Such additives can include wetting agents, emulsifying and suspending agents, salt for influencing osmotic pressure, buffers and/or coloring substances preserving agents, sweetening agents or flavoring agents. The pharmaceutical compositions can also be sterilized if desired.

The route of administration may be any route, which effectively transports the active compound of the invention which inhibits the enzymatic activity of DPP-IV to the appropriate or desired site of action, such as oral, nasal, pulmonary, buccal, subdermal, intradermal, transdermal or parenteral, e.g., rectal, depot, subcutaneous, intravenous, intraurethral, intramuscular, intranasal, ophthalmic solution or an ointment, the oral route being preferred.

If a solid carrier is used for oral administration, the preparation may be tabletted, placed in a hard gelatin capsule in powder or pellet form or it can be in the form of a troche or lozenge. If a liquid carrier is used, the preparation may be in the form of a syrup, emulsion, soft gelatin capsule or sterile injectable liquid such as an aqueous or non-aqueous liquid suspension or solution.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Preferably, the oil or fatty acid is nonvolatile, including natural or synthetic oils, fatty acids, mono-, di- or tri-glycerides.

For injection, the pharmaceutical formulation may also be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these. The compounds may be formulated for parenteral administration by injection such as by bolus injection or continuous infusion. A unit dosage form for injection may be in ampoules or in multi-dose containers.

The formulations of the invention may be designed to provide quick, sustained, or delayed release of the active ingredient after administration to the patient by employing procedures well known in the art. Thus, the pharmaceutical formulations may also be formulated for controlled release or for slow release.

The instant compositions may comprise, for example, micelles or liposomes, or some other encapsulated form, or may be administered in an extended release form to provide a prolonged storage and/or delivery effect. Therefore, the pharmaceutical formulations may be compressed into pellets or cylinders and implanted intramuscularly or subcutaneously as depot injections or as implants such as stents. Such implants may employ known inert materials such as silicones and biodegradable polymers, e.g., polylactide-polyglycolide. Examples of other biodegradable polymers include poly(orthoesters) and poly(anhydrides).

For nasal administration, the preparation may contain a compound of the invention which inhibits the enzymatic activity of DPP-IV, dissolved or suspended in a liquid carrier, in particular an aqueous carrier, for aerosol application. The carrier may contain additives such as solubilizing agents, e.g., propylene glycol, surfactants, absorption enhancers such as lecithin (phosphatidylcholine) or cyclodextrin, or preservatives such as parabenes.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet that may be prepared by conventional tabletting techniques may contain:

| Core: | |
|---|---|
| Active compound (as free compound or salt thereof) | 250 mg |
| Colloidal silicon dioxide (Aerosil) ® | 1.5 mg |
| Cellulose, microcryst. (Avicel) ® | 70 mg |
| Modified cellulose gum (Ac-Di-Sol) ® | 7.5 mg |
| Magnesium stearate | Ad. |
| Coating: | |
| HPMC approx. | 9 mg |
| *Mywacett 9-40 T approx. | 0.9 mg |

*Acylated monoglyceride used as plasticizer for film coating.

The compounds of the invention may be administered to a mammal, especially a human in need of such treatment, prevention, elimination, alleviation or amelioration of the various diseases as mentioned above, e.g., type II diabetes, IGT, IFG, obesity, appetite regulation or as a blood glucose lowering agent, and especially type II diabetes. Such mammals include also animals, both domestic animals, e.g. household pets, farm animals, and non-domestic animals such as wildlife.

The compounds of the invention are effective over a wide dosage range. For example, in the treatment of adult humans, dosages from about 0.05 to about 1000 mg, preferably from about 1 to about 500 mg, per day may be used. A typical dosage is about 10 mg to about 500 mg per day. In choosing a regimen for patients it may frequently be necessary to begin with a higher dosage and when the condition is under control to reduce the dosage. The exact dosage will depend upon the activity of the compound, mode of administration, on the therapy desired, form in which administered, the subject to be treated and the body weight of the subject to be treated, and the preference and experience of the physician or veterinarian in charge. DPP-IV inhibitor activity of the compounds of the invention may be determined by use of an in vitro assay system which measures the potentiation of inhibition of DPP-IV. Inhibition constants (Ki or $IC_{50}$ values) for the DPP-IV inhibitors of the invention may be determined by the method described in the Examples.

Generally, the compounds of the invention are dispensed in unit dosage form comprising from about 0.05 to about 1000 mg of active ingredient together with a pharmaceutically acceptable carrier per unit dosage.

Usually, dosage forms suitable for oral, nasal, pulmonal or transdermal administration comprise from about 0.05 mg to about 1000 mg, preferably from about 0.5 mg to about 500 mg of the compounds admixed with a pharmaceutically acceptable carrier or diluent.

The invention also encompasses prodrugs of a compound of the invention which on administration undergo chemical conversion by metabolic processes before becoming active pharmacological substances. In general, such prodrugs will be functional derivatives of a compound of the invention which are readily convertible in vivo into a compound of the invention. Conventional procedures for the selection and preparation of suitable prodrug derivatives are described, for example, in "Design of Prodrugs", ed. H. Bundgaard, Elsevier, 1985.

In another aspect, there are provided methods of making a pharmaceutical composition of a compound described herein comprising formulating a compound of the invention with a pharmaceutically acceptable carrier or diluent. In some embodiments, the pharmaceutically acceptable carrier or diluent is suitable for oral administration. In some such embodiments, the methods may further comprise the step of formulating the composition into a tablet or capsule. In other embodiments, the pharmaceutically acceptable carrier or diluent is suitable for parenteral administration. In some such embodiments, the methods further comprise the step of lyophilizing the composition to form a lyophilized preparation.

B. Combinations. The compounds of the invention may be used in combination with one or more other types of antidiabetic agents (employed to treat diabetes and related diseases) and/or one or more other types of therapeutic agents which may be administered orally in the same dosage form, in a separate oral dosage form (e.g., sequentially or non-sequentially) or by injection together or separately (e.g., sequentially or non-sequentially).

Accordingly, in another aspect the invention provides pharmaceutical combinations, comprising:
a) a compound of the invention as described herein; and
b) one or more compounds selected from the group consisting of:
  i) Other dipeptidyl peptidase-IV inhibitors;
  ii) Insulin sensitizers selected from the group consisting of PPAR agonists, biguanides, and protein phosphatase-1B inhibitors;
  iii) Insulin or insulin mimetics;
  iv) Sulfonylureas or other insulin secretagogues;
  v) α-glucosidase inhibitors;
  vi) glucagons receptor agonists;
  vii) GLP-1, GLP-1 mimetics, and GLP-1 receptor agonists;

viii) GIP, GIP mimetics, and GIP receptor agonists;
ix) PACAP, PACAP mimetics, and PACAP receptor 3 agonists;
x) GLP-2, GLP-2 mimetics, and GLP-2 receptor agonists;
xi) Cholesterol lowering agents selected from the group consisting of HMG-CoA reductase inhibitors, sequestrants, nicotinyl alcohol, nicotinic acid or a salt thereof, PPARα agonists, PPARα/γ dual agonists, inhibitors of cholesterol absorption, acyl CoA:cholesterol acyltransferase inhibitors, and anti-oxidants;
xii) PPARδ agonists;
xiii) Anti-obesity compounds;
xiv) An ileal bile acid transporter inhibitor;
xv) Anti-inflammatory agents;
xvi) G-CSF, G-CSF mimetics, and G-CSF receptor agonists; and
xvii) EPO, EPO mimetics, and EPO receptor agonists.

Combinations of the invention can further comprise a pharmaceutically acceptable carrier. In some embodiments, the compound of the invention is 90 wt % or more of a single diastereomer or single enantiomer. Alternatively, the compound of the invention can be 91, 92, 93, 94, 95, 96, 97, 98, or 99 wt % or more of a single diastereomer or single enantiomer.

In some embodiments of combinations of the invention the one or more compounds is an antidiabetic agent or antihyperglycemic agent. Further, the one or more compounds can be an antidiabetic agent for treating diabetes and related diseases and an anti-obesity agent, a lipid-modulating agent, or both an anti-obesity agent and a lipid-modulating agent, wherein the antidiabetic agent is not a dipeptidyl peptidase-IV inhibitor. The antidiabetic agent can be 1, 2, 3 or more compounds selected from the group consisting of a biguanide, a sulfonyl urea, a glucosidase inhibitor, a PPAR γ agonist such as a thiazolidinedione, a PPAR α/γ dual agonist, an SGLT2 inhibitor, an aP2 inhibitor, a glycogen phosphorylase inhibitor, an advanced glycosylation end (AGE) products inhibitor, an insulin sensitizer, a glucagon-like peptide-1 (GLP-1) or mimetic thereof, insulin and a meglitinide. Exemplary antidiabetic agents include 1, 2, 3 or more compounds selected from the group consisting of metformin, glyburide, glimepiride, glipyride, glipizide, chlorpropamide, gliclazide, acarbose, miglitol, pioglitazone, troglitazone, rosiglitazone, insulin, Gl-262570, isaglitazone, JTT-501, NN-2344, L895645, YM-440, R-119702, AJ9677, repaglinide, nateglinide, KAD1129, APR-HO39242, GW-409544, KRP297, AC2993, Exendin-4, LY307161, NN2211, and LY315902. The antidiabetic agent may be an oral antihyperglycemic agent such as a biguanides, e.g., metformin or phenformin or salts thereof, such as metformin HCl. In combinations of the invention compounds of the invention are typically present in a weight ratio to the antidiabetic agent of from about 0.01:1 to about 100:1, or from about 0.1:1 to about 5:1.

The use of the compounds of the invention in combination with 1, 2, 3 or more other antidiabetic agents may produce antihyperglycemic results greater than that possible from each of these medicaments alone and greater than the combined additive antihyperglycemic effects produced by these medicaments.

The antidiabetic agent can also be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the γ-cells, with glyburide and glipizide being preferred, which may be administered in the same or in separate oral dosage forms. The compounds of the invention are typically employed in a weight ratio to the sulfonyl urea in the range from about 0.01:1 to about 100:1, preferably from about 0.05:1 to about 5:1.

The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms. The compounds of the invention will be employed in a weight ratio to the glucosidase inhibitor within the range from about 0.01:1 to about 100:1, preferably from about 0.2:1 to about 50:1.

The compounds of the invention may be employed in combination with a PPAR γ agonist such as a thiazolidinedione oral anti-diabetic agent or other insulin sensitizers (which have an insulin sensitivity effect in NIDDM patients) such as troglitazone (Warner-Lambert's Rezulin®, disclosed in U.S. Pat. No. 4,572,912), rosiglitazone (en), pioglitazone (Takeda), Mitsubishi MCC-555 (disclosed in U.S. Pat. No. 5,594,016), Glaxo-Wellcome's GL-262570, englitazone (CP-68722, Pfizer) or darglitazone (CP-86325, Pfizer), isaglitazone (MIT/J&J), JTT-501 (JPNT/P&U), L-895645 (Merck), R-119702 (Sankyo/WL), NN-2344 (Dr. Reddy/NN), or YM-440 (Yamanouchi), preferably rosiglitazone and pioglitazone. The compounds of the invention will be employed in a weight ratio to the thiazolidinedione in an amount within the range from about 0.01:1 to about 100:1, preferably from about 0.1:1 to about 10:1.

Where present, the thiazolidinedione anti-diabetic agent may be employed in amounts within the range from about 0.01 to about 2000 mg/day which may be administered in single or divided doses one to four times per day.

The sulfonyl urea and thiazolidinedione in amounts of less than about 150 mg oral antidiabetic agent may be incorporated in a single tablet with the compounds of the invention.

Where present, metformin, the sulfonyl ureas, such as glyburide, glimepiride, glipyride, glipizide, chlorpropamide and gliclazide and the glucosidase inhibitors acarbose or miglitol or insulin (injectable, pulmonary, buccal, or oral) may be employed in formulations as described above and in amounts and dosing as indicated in the PHYSICIAN'S DESK REFERENCE (PDR). For example, where present, metformin or salt thereof may be employed in amounts within the range from about 500 to about 2500 mg per day which may be administered in single or divided doses one to four times daily.

The compounds of the invention may also be employed in combination with a antihyperglycemic agent such as insulin or with glucagon-like peptide-1 (GLP-1) such as GLP-1(1-36) amide, GLP-1(7-36) amide, GLP-1(7-36) (as disclosed in U.S. Pat. No. 5,614,492 to Habener, disclosure of which is incorporated herein by reference), or a GLP-1 mimic such as AC2993 or Exendin-4 (Amylin) and LY-315902 or LY-307167 (Lilly) and NN2211 (Novo-Nordisk), which may be administered via injection, intranasal, or by transdermal or buccal devices. GLP-1 peptides may be administered in oral buccal formulations, by nasal administration (for example inhalation spray) or parenterally as described in U.S. Pat. No. 5,346,701 (TheraTech), U.S. Pat. Nos. 5,614,492 and 5,631,224 which are incorporated herein by reference.

The antidiabetic agent may also be a PPAR α/γ dual agonist such as AR-HO39242 (Astra/Zeneca), GW-409544 (Glaxo-Wellcome), KRP297 (Kyorin Merck), as well as those disclosed by Murakami et al., "A Novel Insulin Sensitizer Acts As a Coligand for Peroxisome Proliferation—Activated Receptor Alpha (PPAR alpha) and PPAR gamma. Effect on PPAR alpha Activation on Abnormal Lipid Metabolism in Liver of Zucker Fatty Rats," *Diabetes* 47: 1841-47 (1998), and in U.S. application Ser. No. 09/664,598, filed Sep. 18, 2000, the disclosure of which is incorporated herein by reference, employing dosages as set out therein, which compounds designated as preferred are preferred for use herein.

The antidiabetic agent may be an SGLT2 inhibitor, as disclosed in U.S. application Ser. No. 09/679,027, filed Oct. 4, 2000, which is incorporated herein by reference, employing dosages as set out therein. Preferred are the compounds designated as preferred in the above application.

Another antidiabetic agent which may be employed in combination with the DPP-IV inhibitors in accordance with the present invention is an aP2 inhibitor, as disclosed in U.S. application Ser. No. 09/519,079, filed Mar. 6, 2000, which is incorporated herein by reference, employing dosages as set out therein. Preferred are the compounds designated as preferred in the above application.

The antidiabetic agent that may employed with the DPP-IV inhibitors of the invention can be a glycogen phosphorylase inhibitor as disclosed, for instance, in WO 96/39384, WO 96/39385, WO 99/26659, WO 99/43663, WO 2000/47206, EP 978279, EP 1041068, and U.S. Pat. No. 5,952,322 and No. 5,998,463.

The meglitinide which may optionally be employed in combination with the compound of the invention may be repaglinide, nateglinide (Novartis) or KAD1229 (PF/Kissei), with repaglinide being preferred.

The DPP-IV inhibitors of the invention will be employed in a weight ratio to the meglitinide, PPAR γ agonist, PPAR α/γ dual agonist, SGLT2 inhibitor, aP2 inhibitor, or glycogen phosphorylase inhibitor within the range from about 0.01:1 to about 100:1, preferably from about 0.1:1 to about 50:1.

In some combinations of the invention, the lipid-modulating agent or hypolipidemic agent may include 1,2,3 or more MTP inhibitors, HMG CoA reductase inhibitors, squalene synthetase inhibitors, fibric acid derivatives, ACAT inhibitors, lipoxygenase inhibitors, cholesterol absorption inhibitors, ileal Na+/bile acid cotransporter inhibitors, upregulators of LDL receptor activity, ATP citrate lyase inhibitors, cholesteryl ester transfer protein inhibitors, bile acid sequestrants, nicotinic acid and derivatives thereof., or a mixture of any two or more thereof. For example, the lipid-modulating agent can be pravastatin, lovastatin, simvastatin, atorvastatin, cerivastatin, fluvastatin, nisvastatin, visastatin, fenofibrate, gemfibrozil, clofibrate, implitapide, CP-529,414, avasimibe, TS-962, MD-700, LY295427, or a mixture of any two or more thereof. Preferred hypolipidemic agents are pravastatin, lovastatin, simvastatin, atorvastatin, fluvastatin, cerivastatin, atavastatin and ZD-4522. In such combinations the inventive compound can be present in a weight ratio to the lipid-modulating agent from about 0.01 to about 100:1.

MTP inhibitors employed herein include MTP inhibitors disclosed in U.S. Pat. No. 5,595,872, No. 5,739,135, No. 5,712,279, No. 5,760,246, No. 5,827,875, No. 5,885,983, and No. 5,962,440. MTP inhibitors preferred herein are those identified as being preferred in the above referenced patents. Most preferred MTP inhibitors, in accordance with the present invention, are implitapide (Bayer) and those set out in U.S. Pat. No. 5,739,135, No. 5,712,279, and No. 5,760,246. A particularly preferred MTP inhibitor in this context is 9-[4-[4-[[2-(2,2,2-Trifluoroethoxy)-benzoyl]amino]-1-piperidinyl]butyl]-N-(2,2,2,-trifluoroethyl)-9H-fluorene-9-carboxamide.

The hypolipidemic agent may be an HMG CoA reductase inhibitor which includes, but is not limited to, mevastatin and related compounds as disclosed in U.S. Pat. No. 3,983,140, lovastatin (mevinolin) and related compounds disclosed in U.S. Pat No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. No. 5,006,530 and No. 5,177,080, atorvastatin disclosed in U.S. Pat. No. 4,681,893, No. 5,273,995, No. 5,385,929 and No. 5,686,104, atavastatin (Nissan/Sankyo nisvastatin (NK-104)), disclosed in U.S. Pat. No. 5,011,930, and Shionogi-Astra/Zeneca visastatin (ZD-4522), disclosed in U.S. Pat. No. 5,260,440.

The squalene synthetase inhibitors suitable for use herein include, but are not limited to, α-phosphono-sulfonates disclosed in U.S. Pat. No. 5,712,396, those disclosed by Biller et al, J. Med. Chem., 1988, Vol. 11, No. 10, pp 1869-1871, including isoprenoid (phosphinyl-methyl)phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1-40 (1996).

In addition, other squalene synthetase inhibitors suitable for use herein include the terpenoid pyrophosphates disclosed by P. Ortiz de Montellano et al, J. Med. Chem., 1977, 20, 243-249, the famesyl diphosphate analog A and presqualene pyrophosphate (PSQ-PP) analogs as disclosed by Corey and Volante, J. Am. Chem. Soc., 1976, 98, 1291-1293, phosphinylphosphonates reported by McClard, R. W. et al, J.A.C.S., 1987, 10, 5544 and cyclopropanes reported by Capson, T. L., PhD dissertation, June, 1987, Dept. Med. Chem. U of Utah, Abstracts Table of Contents, pp 16, 17, 40-43, 48-51, Summary.

Other hypolipidemic agents suitable for use herein include, but are not limited to, fibric acid derivatives, such as fenofibrate, gemfibrozil, clofibrate, bezafibrate, ciprofibrate, clinofibrate, and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly(diallylmethylamine) derivatives such as disclosed in U.S. Pat. No. 4,759,923, quaternary amine poly(diallyldimethylammonium chloride) and ionenes such as disclosed in U.S. Pat. No. 4,027,009, and other known serum cholesterol lowering agents.

The hypolipidemic agent may be an ACAT inhibitor such as disclosed in 24 DRUGS OF THE FUTURE 9-15 (Avasimibe 1999), "The ACAT inhibitor, Cl-1011 is effective in the prevention and regression of aortic fatty streak area in hamsters", Nicolosi et al, Atherosclerosis (Shannon, Irel). (1998), 137(1), 77-85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16-30; "RP 73163: a bioavailable alkylsulfinyl-diphenylimidazole ACAT inhibitor", Smith, C., et al, Bioorg. Med. Chem. Lett. (1996), 6(1), 47-50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173-98, Publisher: CRC, Boca Raton, Fla.; "ACAT inhibitors: potential anti-atherosclerotic agents", Sliskovic et al, Curr. Med. Chem. (1994), 1(3), 204-25; "Inhibitors of acyl-CoA: cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359-62, or TS-962 (Taisho Pharmaceutical Co. Ltd).

The hypolipidemic agent may be an upregulator of LD2 receptor activity such as MD-700 (Taisho Pharmaceutical Co. Ltd) and LY295427 (Eli Lilly).

The hypolipidemic agent may be a cholesterol absorption inhibitor preferably Schering-Plough's SCH48461 as well as those disclosed in Atherosclerosis 115, 45-63 (1995) and J. Med. Chem. 41, 973 (1998).

The hypolipidemic agent may be an ileal $Na^+$/bile acid cotransporter inhibitor such as disclosed in Drugs of the Future, 24, 425-430 (1999).

The lipid-modulating agent may be a cholesteryl ester transfer protein (CETP) inhibitor such as Pfizer's CP 529,414 (WO/0038722 and EP 818448) and Pharmacia's SC-744 and SC-795.

The ATP citrate lyase inhibitor which may be employed in the combination of the invention may include, for example, those disclosed in U.S. Pat. No. 5,447,954.

The compounds of the invention will be employed in a weight ratio to the hypolipidemic agent (where present), within the range from about 500:1 to about 1:500, preferably from about 100:1 to about 1:100.

The dose administered may be adjusted according to age, weight and condition of the patient, as well as the route of administration, dosage form and regimen and the desired result. The dosages and formulations for the hypolipidemic agent will be as disclosed in the various patents and applications discussed above.

The dosages and formulations for the other hypolipidemic agent to be employed, where applicable, will be as set out in the latest edition of the Physicians' Desk Reference.

For oral administration, a satisfactory result may be obtained employing the MTP inhibitor in an amount within the range of from about 0.01 mg/kg to about 500 mg and preferably from about 0.1 mg to about 100 mg, one to four times daily.

An oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor, for example, pravastatin, lovastatin, simvastatin, atorvastatin, fluvastatin or cerivastatin in dosages employed as indicated in the PHYSICIAN'S DESK REFERENCE, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 5 to about 80 mg, and more preferably from about 10 to about 40 mg.

A preferred oral dosage form, such as tablets or capsules will contain the squalene synthetase inhibitor in an amount of from about 10 to about 500 mg, preferably from about 25 to about 200 mg.

The other hypolipidemic agent may also be a lipoxygenase inhibitor including a 15-lipoxygenase (15-LO) inhibitor such as benzimidazole derivatives as disclosed in WO 97/12615, 15-LO inhibitors as disclosed in WO 97/12613, isothiazolones as disclosed in WO 96/38144, and 15-LO inhibitors as disclosed by Sendobry et al "Attenuation of diet-induced atherosclerosis in rabbits with a highly selective 15-lipoxygenase inhibitor lacking significant antioxidant properties", Brit. J. Pharmacology (1997) 120, 1199-1206, and Cornicelli et al, "15-Lipoxygenase and its Inhibition: A Novel Therapeutic Target for Vascular Disease", Current Pharmaceutical Design, 1999, 5, 11-20.

The compounds of the invention and the hypolipidemic agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

In combinations of the invention the one or more compounds can be an anti-obesity agent selected from a beta 3 adrenergic agonist, a lipase inhibitor, a serotonin (and dopamine) reuptake inhibitor, a thyroid receptor beta compound, an anorectic agent, a fatty acid oxidation upregulator, or a mixture of any two or more thereof. Suitable anti-obesity agents include orlistat, ATL-962, AJ9677, L750355, CP331648, sibutramine, topiramate, axokine, dexamphetamine, phentermine, phenylpropanolamine, famoxin, mazindol, or a mixture of any two or more thereof.

The beta 3 adrenergic agonist which may be optionally employed in combination with a compound of the invention may be AJ9677 (Takeda/Dainippon), L750355 (Merck), or CP331648 (Pfizer) or other known beta 3 agonists as disclosed in U.S. Pat, No. 5,541,204, No. 5,770,615, No. 5,491, 134, No. 5,776,983 and No. 5,488,064, with AJ9677, L750, 355 and CP331648 being preferred.

The lipase inhibitor which may be optionally employed in combination with a compound of the invention may be orlistat or ATL-962 (Alizyme), with orlistat being preferred.

The serotonin (and dopamine) reuptake inhibitor which may be optionally employed in combination with a compound of the invention may be sibutramine, topiramate (Johnson & Johnson) or axokine (Regeneron), with sibutramine and topiramate being preferred.

The thyroid receptor beta compound which may be optionally employed in combination with a compound of the invention may be a thyroid receptor ligand as disclosed in WO97/21993 (U. Cal SF), WO099/00353 (KaroBio) and GB98/284425 (KaroBio), with compounds of the KaroBio applications being preferred.

The anorectic agent which may be optionally employed in combination with a compound of the invention may be dexamphetamine, phentermine, phenylpropanolamine or mazindol, with dexamphetamine being preferred.

The fatty acid oxidation upregulator which may be optionally employed in combination with the compound of the invention can be famoxin (Genset).

The various anti-obesity agents described above may be employed in the same dosage form with the compound of the invention or in different dosage forms, in dosages and regimens as generally known in the art or in the PDR.

In another aspect, pharmaceutical combinations of the invention include a DPP-IV inhibitor of the invention and an agent for treating an agent for treating polycystic ovary syndrome, an agent for treating a growth disorder and/or frailty, an anti-arthritis agent, an agent for preventing or inhibiting allograft rejection in transplantation, an agent for treating autoimmune disease, an anti-AIDS agent, an agent for treating inflammatory bowel disease/syndrome, an agent for treating anorexia nervosa, an anti-osteoporosis agent, an anti-obesity agent or a mixture of any two or more thereof.

The agent for polycystic ovary syndrome which may be optionally employed in combination with the DPP-IV inhibitor of the invention may be 1, 2, or more of gonadotropin releasing hormone (GnRH), leuprolide (Lupron®), Clomid®, Parlodel®, oral contraceptives or insulin sensitizers such as PPAR agonists, or other conventional agents for such use which may be employed in amounts specified in the PDR.

The agent for treating growth disorders and/or frailty which may be optionally employed in combination with the DPP-IV inhibitor of the invention may be 1, 2, or more of a growth hormone or growth hormone secretagogue such as MK-677 (Merck), CP-424,391 (Pfizer), and compounds disclosed in U.S. Ser. No. 09/506,749 filed Feb. 18, 2000, as well as selective androgen receptor modulators (SARMs), which is incorporated herein by reference, which may be employed in amounts specified in the PDR, where applicable.

The agent for treating arthritis which may be optionally employed in combination with the DPP-IV inhibitor of the invention may be 1, 2, or more of aspirin, indomethacin, ibuprofen, diclofenac sodium, naproxen, nabumetone (Relafen®, SmithKline Beecham), tolmetin sodium (Tolectin®, Ortho-McNeil), piroxicam (Feldene®, Pfizer), ketorolac tromethamine (Toradol®, Roche), celecoxib (Celebrex®, Searle), rofecoxib (Vioxx®, Merck) and the like, which may be employed in amounts specified in the PDR.

Conventional agents for preventing allograft rejection in transplantation such as cyclosporin, Sandimmune (Novartis), azathioprine, Imuran (Faro) or methotrexate may be optionally employed in combination with the DPP-IV inhibitor of the invention, which may be employed in amounts specified in the PDR.

Conventional agents for treating autoimmune diseases such as multiple sclerosis and immunomodulatory diseases such as lupus erythematosis, psoriasis, for example, azathioprine, Imuran, cyclophosphamide, NSAIDS such as ibuprofen, cox 2 inhibitors such as Vioxx and Celebrex, glucocorticoids and hydroxychloroquine, may be optionally employed in combination with the DPP-IV inhibitor of the invention, which may be employed in amounts specified in the PDR.

The AIDS agent which may be optionally employed in combination with the DPP-IV inhibitor of the invention may be a non-nucleoside reverse transcriptase inhibitor, a nucleoside reverse transcriptase inhibitor, a protease inhibitor and/or an AIDS adjunct anti-infective and may be 1, 2, or more of dronabinol (Marinol®, Roxane Labs), didanosine (Videx®, Bristol-Myers Squibb), megestrol acetate (Megace®, Bristol-Myers Squibb), stavudine (Zerit®, Bristol-Myers Squibb), delavirdine mesylate (Rescriptor®, Pharmacia), lamivudine/zidovudine (Combivir.™., Glaxo), lamivudine (Epivir.™., Glaxo), zalcitabine (Hivid®), Roche), zidovudine (Retrovir®, Glaxo), indinavir sulfate (Crixivan®, Merck), saquinavir (Fortovase.™., Roche), saquinavir mesylate (Invirase®, Roche), ritonavir (Norvir®, Abbott), nelfinavir (Viracept®, Agouron).

The above anti-AIDS agents may be employed in amounts specified in the PDR.

The agent for treating inflammatory bowel disease or syndrome which may be optionally employed in combination with the DPP-IV inhibitor of the invention may be 1, 2, or more of sulfasalazine, salicylates, mesalamine (Asacol®, P&G) or Zelmac®, (Bristol-Myers Squibb), which may be employed in amounts specified in the PDR or otherwise known in the art.

The agent for treating osteoporosis which may be optionally employed in combination with the DPP-IV inhibitor of the invention may be 1, 2, or more of alendronate sodium (Fosamax®, Merck, tiludronate (Skelid®, Sanofi), etidronate disodium (Didronel®, P&G), raloxifene HCl (Evista®, Lilly), which may be employed in amounts specified in the PDR.

In carrying out the methods of the invention, a pharmaceutical composition may be employed containing the compounds of the invention, with or without another antidiabetic agent and/or other type therapeutic agent, in association with a pharmaceutical vehicle or diluent. The pharmaceutical composition can be formulated employing conventional solid or liquid vehicles or diluents and pharmaceutical additives of a type appropriate to the mode of desired administration. The compounds can be administered to mammalian species including humans, monkeys, dogs, etc. by an oral route, for example, in the form of tablets, capsules, granules or powders, or they can be administered by a parenteral route in the form of injectable preparations. The dose for adults is preferably between 10 and 1,000 mg per day, which can be administered in a single dose or in the form of individual doses from 1-4 times per day.

A typical capsule for oral administration contains compounds of the invention (250 mg), lactose (75 mg) and magnesium stearate (15 mg). The mixture is passed through a 60 mesh sieve and packed into a No. 1 gelatin capsule. A typical injectable preparation is produced by aseptically placing 250 mg of compounds of the invention into a vial, aseptically freeze-drying and sealing. For use, the contents of the vial are mixed with 2 mL of physiological saline, to produce an injectable preparation.

Definitions

The term "DPP-IV" denotes dipeptidyl peptidase IV (EC 3.4.14.5; DPP-IV), also known as "CD-26." DPP-IV preferentially cleaves a dipeptide from the N terminus of a polypeptide chain containing a proline or alanine residue in the penultimate position.

The term "diabetes and related diseases" refers to Type II diabetes, Type I diabetes, impaired glucose tolerance, obesity, hyperglycemia, Syndrome X, dysmetabolic syndrome, diabetic complications, diabetic dyslipidemia, hyperinsulinemia, and the like.

The conditions, diseases and maladies collectively referred to as "diabetic complications" include retinopathy, neuropathy and nephropathy, and other known complications of diabetes.

The term "other type(s) of therapeutic agents" as employed herein refers to one or more antidiabetic agents (other than DPP-IV inhibitors of the invention), one or more anti-obesity agents, and/or one or more lipid-modulating agents (including anti-atherosclerosis agents), and/or one or more agents for treating polycystic ovary syndrome, one or more agents for treating growth disorders, one or more agents for treating frailty, one or more agents for treating arthritis, one or more agents for preventing allograft rejection in transplantation, one or more agents for treating autoimmune diseases, one or more anti-AIDS agents, one or more anti-osteoporosis agents, one or more agents for treating immunomodulatory diseases, one or more agents for treating chronic inflammatory bowel disease or syndrome and/or one or more agents for treating anorexia nervosa.

The term "lipid-modulating" agent as employed herein refers to agents which lower LDL and/or raise HDL and/or lower triglycerides and/or lower total cholesterol and/or other known mechanisms for therapeutically treating lipid disorders.

The term "treatment" is defined as the management and care of a patient for the purpose of combating the disease, condition, or disorder and includes administering a compound of the present invention to prevent the onset of the symptoms or complications, or alleviating the symptoms or complications, or eliminating the disease, condition, or disorder.

"Treating" within the context of the instant invention means an alleviation of symptoms associated with a disorder or disease, or inhibition of further progression or worsening of those symptoms, or prevention or prophylaxis of the disease or disorder. Similarly, as used herein, an "effective amount" or a "therapeutically effective amount" of a compound of the invention refers to an amount of the compound that alleviates, in whole or in part, symptoms associated with the disorder or condition, or halts further progression or worsening of those symptoms, or prevents or provides prophylaxis for the disorder or condition. A "therapeutically effective amount" refers to an amount effective, at dosages and for periods of time necessary, to achieve the desired therapeutic result by inhibition of DPP-IV activity. A therapeutically effective amount is also one in which any toxic or detrimental effects of compounds of the invention are outweighed by the therapeutically beneficial effects. For example, in the context of treating diabetes and related diseases, a therapeutically effective amount of a DPP-IV inhibitor of the invention is an amount sufficient to control blood glucose levels.

The term "beta cell degeneration" is intended to mean loss of beta cell function, beta cell dysfunction, and death of beta cells, such as necrosis or apoptosis of beta cells.

All chiral, diastereomeric, racemic forms of a structure are intended, unless the specific stereochemistry or isomeric form is specifically indicated. Compounds used in the present invention include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these are all within the scope of the invention.

The term "amino protecting group" or "N-protected" as used herein refers to those groups intended to protect an amino group against undesirable reactions during synthetic procedures and which can later be removed to reveal the amine. Commonly used amino protecting groups are disclosed in *Protective Groups in Organic Synthesis*, Greene, T. W.; Wuts, P. G. M., John Wiley & Sons, New York, N.Y., (3rd Edition, 1999). Amino protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; acyloxy groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. Amine protecting groups also include cyclic amino protecting groups such as phthaloyl and dithiosuccinimidyl, which incorporate the amino nitrogen into a heterocycle. Typically, amino protecting groups include formyl, acetyl, benzoyl, pivaloyl, t-butylacetyl, phenylsulfonyl, Alloc, Teoc, benzyl, Fmoc, Boc and Cbz. It is well within the skill of the ordinary artisan to select and use the appropriate amino protecting group for the synthetic task at hand.

In general, "substituted" refers to an organic group as defined below in which one or more bonds to a hydrogen atom contained therein are replaced by a bond to non-hydrogen or non-carbon atoms such as, but not limited to, a halogen (i.e., F, Cl, Br, and I); an oxygen atom in groups such as hydroxyl groups, alkoxy groups, aryloxy groups, aralkyloxy groups; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, N-oxides, hydrazides, azides, and enamines; and other heteroatoms in various other groups. Substituted alkyl, alkenyl, alkynyl, cycloalkyl, and cycloalkenyl groups as well as other substituted groups also include groups in which one or more bonds to a carbon(s) or hydrogen(s) atom are replaced by one or more bonds, including double or triple bonds, to a heteroatom such as, but not limited to, oxygen in carbonyl (oxo), carboxyl, ester, amide, imide, urethane, and urea groups; and nitrogen in imines, hydroxyimines, oximes, hydrazones, amidines, guanidines, and nitriles.

Substituted ring groups such as substituted aryl, heterocyclyl and heteroaryl groups also include rings and fused ring systems in which a bond to a hydrogen atom is replaced with a bond to a carbon atom. Therefore, substituted aryl, heterocyclyl and heteroaryl groups may also be substituted with alkyl, alkenyl, and alkynyl groups as defined below.

Alkyl groups include straight chain and branched alkyl groups and cycloalkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, isobutyl, sec-butyl, t-butyl, neopentyl, isopentyl, and 2,2-dimethylpropyl groups. Representative substituted alkyl groups may be substituted one or more times with any of the groups listed above, for example, amino, hydroxy, cyano, carboxy, nitro, thio, alkoxy, and halogen groups.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which may be substituted with, for example, amino, hydroxy, cyano, carboxy, nitro, thio, alkoxy, and halogen groups.

(Cycloalkyl)alkyl groups are alkyl groups as defined above in which a hydrogen or carbon bond of the alkyl group is replaced with a bond to a cycloalkyl group as defined above.

Alkenyl groups include straight and branched chain and cyclic alkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to vinyl, —CH═CH(CH$_3$), —CH═C(CH$_3$)$_2$, —C(CH$_3$)═CH$_2$, —C(CH$_3$)═CH(CH$_3$), —C(CH$_2$CH$_3$)═CH$_2$, cyclohexenyl, cyclopentenyl, cyclohexadienyl, butadienyl, pentadienyl, and hexadienyl among others.

Cycloalkenyl groups include cycloalkyl groups having at least one double bond between 2 carbons. Thus for example, cycloalkenyl groups include but are not limited to cyclohexenyl, cyclopentenyl, cyclohexadienyl, butadienyl, pentadienyl, and hexadienyl groups.

(Cycloalkenyl)alkyl groups are alkyl groups as defined above in which a hydrogen or carbon bond of the alkyl group is replaced with a bond to a cycloalkenyl group as defined above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to —C═CH, —C═C(CH$_3$), —C═C(CH$_2$CH$_3$), —CH$_2$C↑CH, —CH$_2$C═C(CH$_3$), and —CH$_2$C═C(CH$_2$CH$_3$) among others.

Aryl groups are cyclic aromatic hydrocarbons that do not contain heteroatoms. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain 6-14 carbons in the ring portions of the groups. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halogen groups, bonded to one of the ring members. Rather, groups such as tolyl are referred to as substituted aryl groups. Representative substituted aryl groups may be mono-substituted or substituted more than once, such as, but not limited to, 2-, 3-, 4-, 5-, or 6-substituted phenyl or naphthyl groups, which may be substituted with groups such as those listed above.

Aralkyl groups are alkyl groups as defined above in which a hydrogen or carbon bond of an alkyl group is replaced with a bond to an aryl group as defined above. Representative aralkyl groups include benzyl and phenylethyl groups and fused (cycloalkylaryl)alkyl groups such as 4-ethyl-indanyl.

Heterocyclyl groups include aromatic and non-aromatic ring compounds containing 3 or more ring members, of which, one or more is a heteroatom such as, but not limited to, N, O, and S. In some embodiments, heterocyclyl groups include 3 to 20 ring members, whereas other such groups have 3 to 15 ring members. The phrase "heterocyclyl group" includes fused ring species including those comprising fused aromatic and non-aromatic groups. The phrase also includes polycyclic ring systems containing a heteroatom such as, but not limited to, quinuclidyl. However, the phrase does not include heterocyclyl groups that have other groups, such as alkyl or halogen groups, bonded to one of the ring members. Rather, these are referred to as "substituted heterocyclyl groups". Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups may be mono-substituted or substituted more than once, such as, but not limited to, piperidinyl or quinolinyl groups, which are 2-, 3-, 4-, 5-, or 6-substituted, or disubstituted with groups such as those listed above.

Heteroaryl groups are aromatic ring compounds containing 5 or more ring members, of which, one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Although the phrase "heteroaryl groups" includes fused ring compounds such as indolyl and 2,3-dihydro indolyl, the phrase does not include heteroaryl groups that have other groups bonded to one of the ring members, such as alkyl groups. Rather, heteroaryl groups with such substitution are referred to as "substituted heteroaryl groups". Representative substituted heteroaryl groups may be substituted one or more times with groups such as those listed above.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (I-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl(2-thiazolyl, 4-thiazolyl, 5-thiazolyl), pyridyl(2-pyridyl, 3-pyridyl, 4-pyridyl), pyrimidinyl(2-pyrimidinyl, 4-pyrimidinyl, 5-pyrimidinyl, 6-pyrimidinyl), pyrazinyl, pyridazinyl(3-pyridazinyl, 4-pyridazinyl, 5-pyridazinyl), quinolyl(2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl, 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole(1-indazolyl, 3-indazolyl, 4-indazolyl, 5-indazolyl, 6-indazolyl, 7-indazolyl), benzimidazolyl(1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl(1-benzothiazolyl, 2-benzothiazolyl, 4-benzothiazolyl, 5-benzothiazolyl, 6-benzothiazolyl, 7-benzothiazolyl), carbazolyl(1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

Heterocyclylalkyl groups are alkyl groups as defined above in which a hydrogen or carbon bond of an alkyl group is replaced with a bond to a heterocyclyl group as defined above. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

Heteroaralkyl groups are alkyl groups as defined above in which a hydrogen or carbon bond of an alkyl group is replaced with a bond to a heteroaryl group as defined above.

The term "alkoxy" refers to an oxygen atom connected to an alkyl group as defined above. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like.

The terms "aryloxy" and "arylalkoxy" refer to, respectively, an aryl group bonded to an oxygen atom and an aralkyl group bonded to the oxygen atom at the alkyl. Examples include but are not limited to phenoxy, naphthyloxy, and benzyloxy.

The term "alkanoyl", alone or as part of another group, refers to alkyl linked to a carbonyl group.

The term "amine" (or "amino") includes primary, secondary, and tertiary amines having, e.g., the formula —$NR^{30}R^{31}$. $R^{30}$ and $R^{31}$ at each occurrence are independently hydrogen, or a substituted or unsubstituted alkyl, alkenyl, alkynyl, cycloalkyl, cycloalkenyl, aryl, arlkyl, heterocyclyl or heterocyclylalkyl group as defined herein. Amines thus include but are not limited to —$NH_2$, alkylamines, dialkylamines, arylamines, alkylarylamines, diarylamines, aralkylamines, heterocyclylamines and the like.

The term "amide" (or "amido") includes C- and N-amide groups, i.e., —$C(O)NR^{32}R^{33}$, and —$NR^{32}C(O)R^{33}$ groups, respectively. $R^{32}$ and $R^{33}$ are independently hydrogen, or a substituted or unsubstituted alkyl, alkenyl, alkynyl, cycloalkyl, cycloalkenyl, aryl, arlkyl, heterocyclyl or heterocyclylalkyl group as defined herein. Amide groups therefore include but are not limited to carbamoyl groups (—$C(O)NH_2$) and formamide groups (—$NHC(O)H$).

The term "urethane" (or "carbamyl") includes N- and O-urethane groups, i.e., —$NR^{34}C(O)OR^{35}$ and —$OC(O)NR^{34}R^{35}$ groups, respectively. $R^{34}$ and $R^{35}$ are independently hydrogen, or a substituted or unsubstituted alkyl, cycloalkyl, aryl, arlkyl, or heterocyclyl group as defined herein.

The term "sulfonamide" (or "sulfonamido") includes S- and N-sulfonamide groups, i.e., —$SO_2NR^{36}R^{37}$ and —$NR^{36}SO_2R^{37}$ groups, respectively. $R^{36}$ and $R^{37}$ are independently hydrogen, or a substituted or unsubstituted alkyl, cycloalkyl, aryl, arlkyl, or heterocyclyl group as defined herein. Sulfonamide groups therefore include but are not limited to sulfamoyl groups (—$SO_2NH_2$).

The term "amidine" or "amidino" includes groups of the formula —$C(NR^{38})NR^{39}R^{40}$. $R^{38}$, $R^{39}$, and $R^{40}$ are independently H, an amino protecting group, or a substituted or unsubstituted alkyl, cycloalkyl, aryl, aralkyl, or heterocyclyl group as defined herein. Typically, an amidino group is —$C(NH)NH_2$.

The term "guanidine" or "guanidino" includes groups of the formula —$NR^{41}C(NR^{42})NR^{43}R^{44}$. $R^{41}$, $R^{42}$, $R^{43}$, and $R^{44}$ are independently H, an amino protecting group, or a substituted or unsubstituted alkyl, cycloalkyl, aryl, aralkyl, or heterocyclyl group as defined herein. Typically, a guanidino group is —$NHC(NH)NH_2$.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present invention, thus generally described, will be understood more readily by reference to the following examples, which are provided by way of illustration and are not intended to be limiting of the present invention.

EXAMPLES

A further detailed description of the invention is given with reference to the following non-limiting examples.

Example 1

Synthesis of 6-Amino-5-oxo-hexahydro-pyrrolo[2,1-b]thiazole-3-carbonitrile

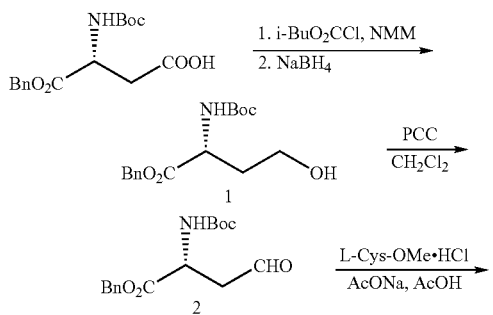

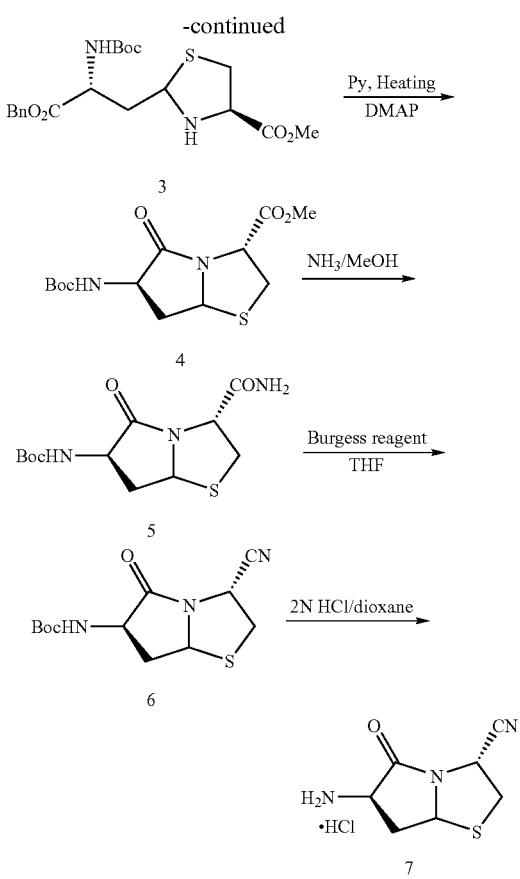

2-tert-Butoxycarbonylamino-4-hydroxy-butyric acid benzyl ester (1). To a solution of D-Boc-Asp-OBzl (2 g, 6.18 mmol) and NMM (0.62 g, 6.18 mmol) in anhydrous DME (10 mL) at −15° C. was added i-BuO$_2$CCl (0.84 g, 6.18 mmol) slowly. After ten minutes, the precipitated N-methyl morpholine hydrochloride was filtered off, and washed with DME. The filtrate was combined with the washings in a large flask. A solution of sodium borohydride (0.35 g, 9.27 mmol) in water (5 mL) was added right away, producing a strong evolution of gas, followed by water immediately afterwards. The solution was extracted with ethyl acetate. The organic layers were combined and dried over Na$_2$SO$_4$. The combined organic layers were evaporated to dryness below 30° C. and then the crude product (1.65 g, 86 %) was obtained and used directly in the next step. $^1$H NMR (400 MHz, CDCl$_3$) δ1.43 (s, 9 H), 1.63 (m, 1 H), 2.15 (m, 1H), 3.62-3.69 (m, 2 H), 4.53 (m, 1 H), 5.18 (m, 2 H), 5.41 (d, 1 H), 7.35 (m, 5 H).

2-tert-Butoxycarbonylamino-4-oxo-butyric acid benzyl ester (2). To a solution of 1 (1.65 g, 5.50 mmol) in CH$_2$Cl$_2$ (4 mL) was added 4 Å molecular sieves (4.5 g) and PCC (2.36 g, 11 mmol). Then the mixture was stirred for 2 hours, filtered through silica gel column until the filtrate was nearly colorless. The filtrate was evaporated to dryness and the crude product (1.4 g, 82%) was obtained and was used directly in the next step. $^1$H NMR (400 MHz, CDCl$_3$) δ1.43 (s, 9 H), 2.97-3.16 (m, 2 H), 4.63 (s, 1H), 5.17 (s, 2 H), 5.40 (d, 1 H), 7.33 (m, 5 H), 9.71 (s, 1 H).

2-(2-Benzyloxycarbonyl-2-tert-butoxycarbonylamino-ethyl)-thiazolidine-4-carboxylic acid methyl ester (3). To a solution of 2 (0.7 g, 2.25 mmol), AcOH (0.14 g, 2.25 mmol), AcONa (0.38 g, 4.50 mmol) in ethanol and water (10:1, 11 mL) was added L-Cys-OMe.HCl (0.39 g, 2.25 mmol). After being stirred overnight, the mixture was poured into 100 mL water, extracted with ethyl acetate, and the organic phase was dried and concentrated to give an oily crude product (0.8 g, 82%), which was used directly in the next step. $^1$H NMR (400 MHz, CDCl$_3$) δ1.43 (s, 9 H), 1.95-2.15 (m, 2 H), 2.29-2.41 (m, 1H), 2.87 (m, 1 H), 3.68 (m, 1 H), 3.77 (s, 3 H), 3.96 (m, 0.6 H), 4.50 (m, 1 H), 4.70 (m, 0.4 H), 5.12-5.23 (m, 2 H), 5.35 (d, 0.4 H), 5.75 (d, 0.6 H), 7.36 (m, 5H).

6-tert-Butoxycarbonylamino-5-oxo-hexahydro-pyrrolo[2,1-b]thiazole-3-carboxylic acid methyl ester (4). To a solution of 3 (1.4 g, 3.3 mmol) in 20 mL of pyridine was added 0.1 g DMAP and the mixture was refluxed overnight. After removal of the pyridine, the residue was partitioned between water and ethyl acetate. The organic phase was dried, concentrated and purified by column chromatography on silica gel to afford the pure product (0.5 g, 48%) $^1$H NMR (400 MHz, CDCl$_3$) δ1.44 (s, 9 H), 2.01 (m, 1 H), 3.19 (m, 1H), 3.77 (d, 3 H), 4.12 (m, 1 H), 5.08-5.16 (m, 3 H).

(3-Carbamoyl-5-oxo-hexahydro-pyrrolo[2,1-b]thiazol-6-yl)-carbamic acid tert-butyl ester (5). Compound 4 (0.5 g, 1.58 mmol) was treated with NH$_3$/MeOH (20 mL) at room temperature and stirred overnight. The crude product was obtained by evaporation and used directly in the next step.

(3-Cyano-5-oxo-hexahydro-pyrrolo[2,1-b]thiazol-6-yl)-carbamic acid tert-butyl ester (6). Burgess reagent (0.8 g, 3.3 mmol) was added in portions to a solution of 5 (0.5 g, 1.58 mmol) in dry THF (20 mL) at room temperature, and was stirred overnight. The mixture was washed with water (20 mL), dried over Na$_2$SO$_4$, concentrated and purified by column chromatography on silica gel to produce compound 6 (0.2 g, 50%) $^1$H NMR (400 MHz, CDCl$_3$) δ1.44 (s, 9 H), 2.08-2.11 (m, 1 H), 3.17-3.21 (m, 1H), 3.68 (d, 2 H), 4.50-4.60 (m, 1 H), 5.07 (s, 1 H), 5.14 (t, 1 H), 5.37 (t, 1 H).

6-Amino-5-oxo-hexahydro-pyrrolo[2,1-b]thiazole-3-carbonitrile (7). Compound 6 (0.6 g, 2.12 mmol) was dissolved in 15 mL 2N HCl/dioxane with stirring. After 2 h, many white solid formed. The above clear liquid was removed and another 20 mL dry ethyl ether was added, stirred and then discarded. The product 7 (0.12 g, 26%) was obtained and dried under reduced pressure. $^1$H NMR (400 MHz, CDCl$_3$) δ 1.17 (m, 1 H), 2.05-2.15 (m, 1.5 H), 3.10-3.20 (m, 1.5H), 3.40-3.50 (m, 3.5 H), 4.40-4.55 (m, 1.5 H), 4.95 (m, 1 H), 5.22 (m, 1 H), 5.31 (m, 2 H), 5.54 (m, 1 H).

Example 2

The following scheme illustrates the synthesis of hexahydropyrrolothiazoles alkylated at the 6-position.

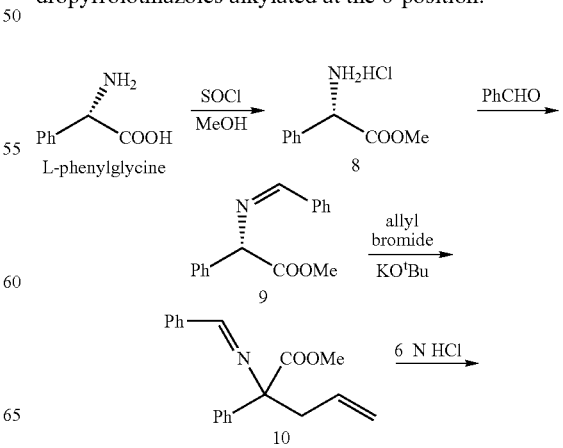

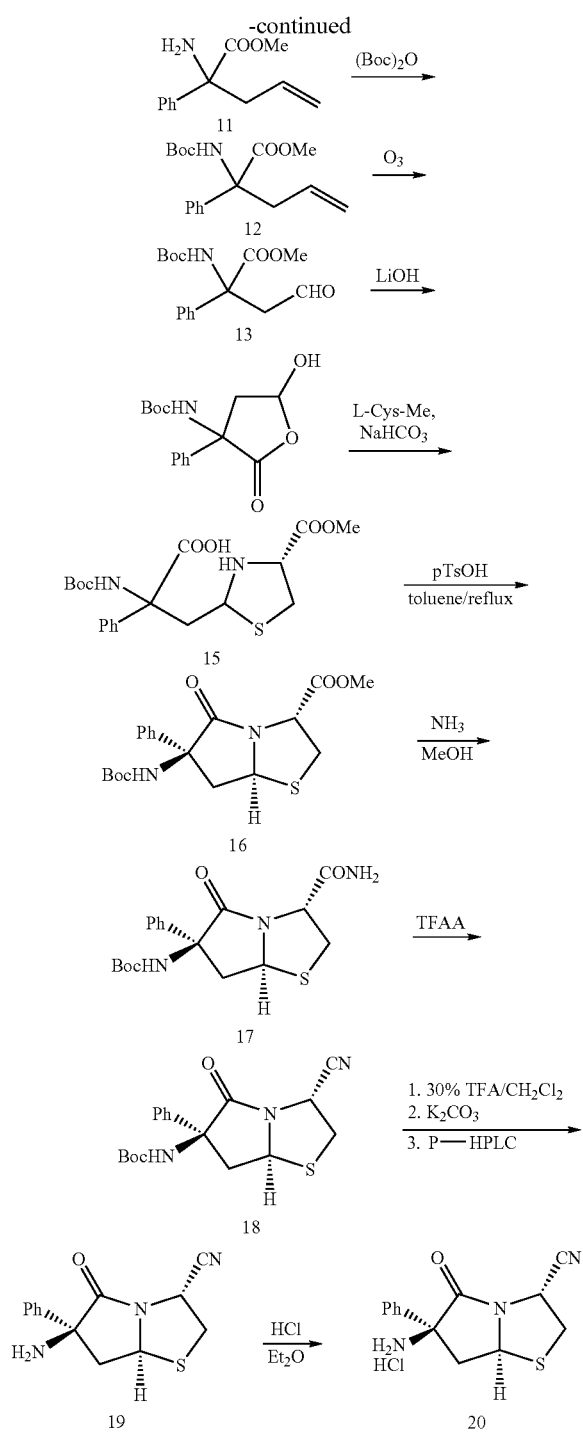

After stirring for 30 min, benzaldehyde (21.2 g, 0.2 mol) was added dropwise, followed by the addition of MgSO$_4$ (240 g, 2 mol). The mixture was stirred overnight. After filtration, the filtrate was evaporated to give compound 9 (49 g, 96.8%). $^1$H NMR (400 MHz, CDCl$_3$) δ 3.72 (s, 3 H), 5.22 (s, 1 H), 7.30-7.39 (m, 6 H), 7.53-7.56 (m, 2 H), 7.82-7.85 (m, 2 H), 8.34 (s, 1 H).

2-Amino-2-phenyl-pent-4-enoic acid methyl ester (11). To a solution of t-BuOK (25.76 g, 0.23 mol) in THF (400 mL) at room temperature was added the solution of compound 9 (49 g, 0.19 mol) in THF (200 mL) slowly. After stirring for 1 h, the solution of allyl bromide (27.9 g, 0.23 mol) in THF (100 mL) was added dropwise to the resulting mixture. After stirring overnight, the solvent was removed in vacuo and ethyl acetate was added, followed by the filtration. Then the filtrate was concentrated to afford 50.5 g compound 10, which was identified by $^1$H NMR. To the solution of compound 10 in 100 mL ethyl acetate was added 6N HCl (200 mL) and the mixture was stirred for one hour. After separation, the aqueous phase was adjusted to pH=9-10 and extracted with ethyl acetate three times. The combined organic layers were dried and evaporated to afford compound 11 (30 g, 63.6%). $^1$H NMR (400 MHz, CDCl$_3$) δ 2.62-2.69 (dd, J=10.4, 18.0 Hz, 1 H), 2.99-3.16 (dd, J=10.4, 13.6 Hz, 1 H), 3.71 (s, 3 H), 5.15-5.27 (m, 2 H), 5.62-5.78 (m, 1 H), 7.28-7.39 (m, 4 H), 7.48-7.53 (m, 1 H).

2-tert-Butoxycarbonylamino-2-phenyl-pent-4-enoic acid methyl ester (12). The solution of 11 (30 g, 0.15 mol) and Boc2O (32 g, 0.165 mol) in THF (300 mL) was heated to reflux overnight. After concentration, the residue was purified by column chromatography on silica gel (petroleum ether: ethyl acetate, 10:1) to give compound 12 (40 g, 87.4%). $^1$H NMR (400 MHz, CDCl3) δ 1.50 (s, 9 H), 3.15-3.28 (m, 1 H), 3.39-3.52 (m, 1 H), 3.71 (s, 3 H), 5.13-5.19 (m, 2 H), 5.60-5.75 (m, 1 H), 6.05 (bs, 1 H), 7.33-7.48 (m, 5 H).

2-tert-Butoxycarbonylamino-4-oxo-2-phenyl-butyric acid methyl ester (13). The solution of compound 12 (30.5 g, 0.1 mol) in CH$_2$Cl$_2$ (300 mL) at −78° C. was bubbled with O$_3$ until the solution turned gray-blue. Then PPh$_3$ (40 g, 0.15 mol) was added slowly to quench the reaction. After concentration, the residue was purified by column chromatography on silica gel (PE: EA=10:1) to give compound 13 (11 g, 35.8%). $^1$H NMR (400 MHz, CDCl$_3$) δ 1.37 (s, 9 H), 3.57-3.61 (d, 1 H, J=18 Hz), 3.71 (s, 3H), 3.98-4.12 (m, 1 H), 6.16 (bs, 1 H), 7.31-7.43 (m, 5 H), 9.74 (s, 1H).

(5-Hydroxy-2-oxo-3-phenyl-tetrahydro-furan-3-yl)-carbamic acid tert-butyl ester (14). To a solution of compound 13 (6.14 g, 20 mmol) in THF (50 mL), 3N LiOH solution (20 mL, 60 mmol) was added. After stirring for 1 h, the resulting mixture was adjusted to pH=5-6 using 1N HCl, and extracted with ethyl acetate. The combined organic phases were concentrated to afford compound 14 (5.6 g, 95.6%). $^1$H NMR (400 MHz, CDCl$_3$) δ 1.43 (s, 9 H), 2.85-2.87 (m, 1 H), 3.17-3.19 (m, 1 H), 5.74-6.11 (bs, 2 H), 7.34-7.46 (m, 5 H).

2-(2-tert-Butoxycarbonylamino-2-carboxy-2-phenyl-ethyl)-thiazolidine-4-carboxylic acid methyl ester (15). To a solution of compound 14 (5.6 g, 19.1 mmol) in EtOH (80 mL) was added 1 M aq. NaHCO$_3$ solution (19.1 mL, 19.1 mmol), followed by the addition of L-Cys-OMe.HCl (3.3 g 19.1 mmol). The pH value of the resulting mixture was adjusted to 6.5 with 1 M NaHCO$_3$ solution. After stirring overnight, the mixture was poured into water, extracted with ethyl acetate, and the combined organic phases were dried over Na$_2$SO$_4$ and concentrated to afford product 15 (7 g, 51.1%). MS (M+1): 411. This product was used in the next step without further purification.

Amino-phenyl-acetic acid methyl ester hydrochloride salt (8). To a stirred solution of (S)-phenylglycine (50 g, 0.3 mol) in MeOH (500 mL) at 0° C. was added thionyl chloride (42.84 g, 0.36 mol) dropwise. After stirring for 2 h, the solvent was concentrated, and the precipitated solid was washed with diethyl ether to afford product 8 (65 g, 97.6%). $^1$H NMR (400 MHz, D$_2$O) δ 3.70 (s, 3 H), 5.17 (s, 1 H), 7.35-7.41 (m, 5 H).

(Benzylidene-amino)-phenyl-acetic acid methyl ester (9). To a solution of 8 (40.3 g, 0.2 mol) in dichloromethane (600 mL) was added triethyl amine (24.24 g, 0.24 mol) dropwise.

6-tert-Butoxycarbonylamino-5-oxo-6-phenyl-hexahydro-pyrrolo[2,1-b]thiazole-3-carboxylic acid methyl ester (16). To a solution of compound 15 (3 g, 7.3 mmol) and p-TsOH.H$_2$O (0.3 g, 1.6 mmol) in toluene (150 mL) was heated to reflux for 1 h. The solution was washed with NaHCO$_3$ solution and brine, dried over Na$_2$SO$_4$. After concentration, the residue was purified by column chromatography on silica gel (PE: EA=10:1) to give compound 16 (660 mg, 23.1%). $^1$H NMR (400 MHz, CDCl$_3$) δ1.41 (s, 9 H), 3.04-3.07 (m, 1 H), 3.24-3.37 (m, 1 H), 3.39-3.41 (m, 1 H), 3.48-3.50 (m, 1 H), 3.74 (s, 3 H), 5.04 (bs, 1 H), 5.25 (bs, 1 H), 5.42 (bs, 1 H), 7.31-7.40 (m, 3H), 7.53-7.54 (m, 2H). MS (M+): 393. The stereochemistry was identified by NOE experiment.

(3-Carbamoyl-5-oxo-6-phenyl-hexahydro-pyrrolo[2,1-b]thiazol-6-yl)-carbamic acid tert-butyl ester (17). To a solution of compound 16 (500 mg, 1.28 mmol) in methanol (10 mL) was added NH$_3$-MeOH (10 mL) at room temperature and stirred for 2 h. The solvent was removed in vacuo and afford compound 17 (470 mg, 97.4%). $^1$H NMR (400 MHz, CDCl$_3$) δ1.42 (s, 9 H), 3.05-3.08 (m, 1 H), 3.35-3.37 (m, 1 H), 3.37-3.49 (m, 1 H), 3.75-3.80 (m, 1 H), 4.89 (bs, 1 H), 4.98 (bs, 1 H), 5.43 (bs, 2 H), 6.57 (bs, 1 H), 7.37-7.50 (m, 5 H). MS (M+1): 378.

(3-Cyano-5-oxo-6-phenyl-hexahydro-pyrrolo[2,1-b]thiazol-6-yl)-carbamic acid tert-butyl ester (18). To a solution of compound 17 (380 mg, 1.0 mmol) in CH$_2$Cl$_2$ (50 mL) was added TFAA (252 uL, 1.2 mmol) dropwise at room temperature, followed by the addition of Et$_3$N (404 mg, 4 mmol). After stirring for 1 h, the mixture was washed with brine, dried over Na$_2$SO$_4$. After concentration, the residue was purified by column chromatography on silica gel (PE: EA=15:1) to give compound 18 (300 mg, 83.6%). $^1$H NMR (400 MHz, CDCl$_3$) δ 1.40 (s, 9 H), 3.26-3.27 (m, 1 H), 3.30-3.31 (m, 1 H), 3.31-3.34 (m, 1 H), 3.43-3.47 (m, 1 H), 5.06 (bs, 1 H), 5.22 (bs, 1H), 5.50 (bs, 1H), 7.37-7.49 (m, 5H). MS (M+1): 360.

6-Amino-5-oxo-6-phenyl-hexahydro-pyrrolo[2,1-b]thiazole-3-carbonitrile hydrochloride salt (20). To a solution of compound 18 (300 mg, 0.84 mmol) in CH$_2$Cl$_2$ (3 mL) was added the solution of TFA (0.9 mL) in CH$_2$Cl$_2$ (3 mL) dropwise at room temperature. After the resulting solution was stirred for 1 h, a saturated aqueous solution of K$_2$CO$_3$ was used to adjust to pH=9. Dichloromethane was used to extract three times and the combined organic layers were washed with brine, dried and concentrated. The residue was purified by P-HPLC to afford product 19 (free base) (30 mg, 13.9%). 1H NMR (400 MHz, CDCl$_3$) δ 2.88-2.95 (m, 1 H), 3.24-3.36 (m, 2 H), 3.52-3.59 (m, 1 H), 5.02-5.09 (m, 1 H), 5.40-5.45 (m, 1H), 7.35-7.60 (m, 5H). MS (M+1): 260;

The solution of compound 19 (30 mg, 0.12 mmol) in 1 mL CH$_2$Cl$_2$ and 5 mL Et$_2$O was bubbled with HCl gas until white solid precipitated. After standing for 2 hrs, the solvent was discarded and it afford compound 20 (18 mg, 52.9%). $^1$H NMR (400 MHz, D$_2$O) δ 2.48-2.55 (m, 1 H), 3.34-3.36 (m, 1 H), 3.45-3.46 (m, 2 H), 5.09-5.14 (m, 1 H), 5.42-5.46 (m, 1H), 7.40-7.49 (m 5H). MS (M+): 260.

Example 3

The following scheme illustrates an alternative synthesis of hexahydropyrrolothiazoles alkylated at the 6-position.

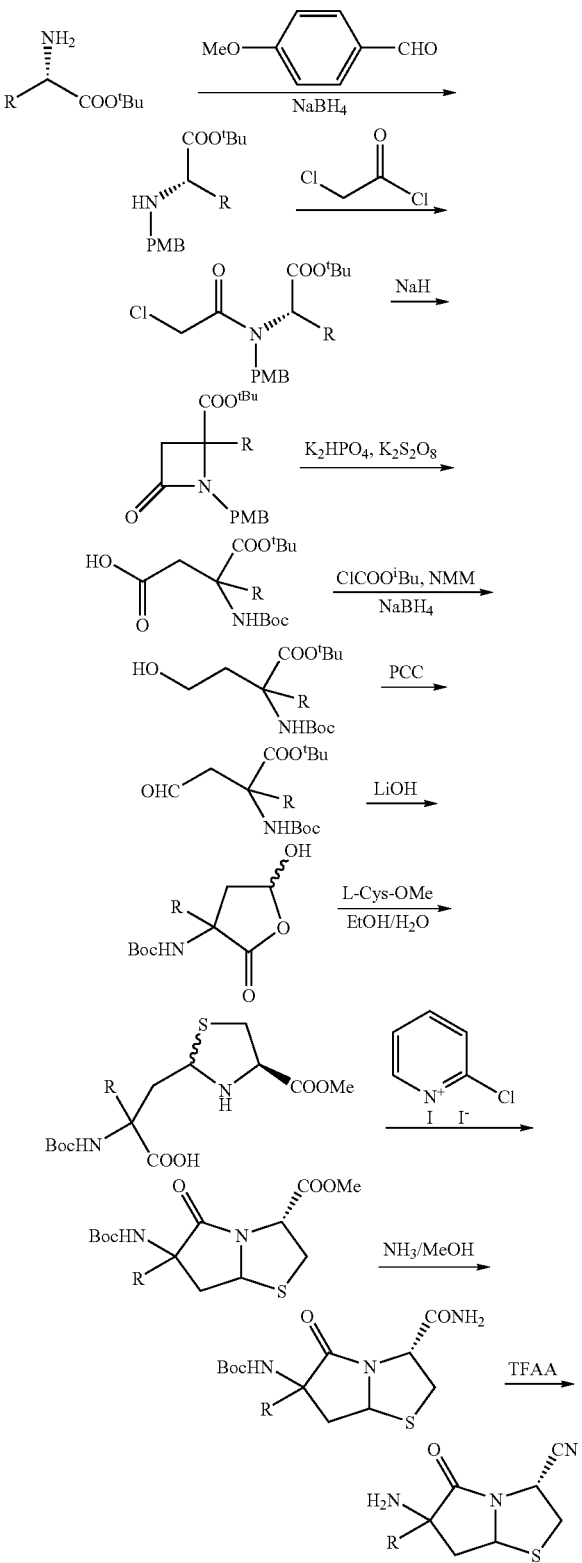

Example 4
The following scheme illustrates the synthesis of N-substituted hexahydro-pyrrolothiazoles.
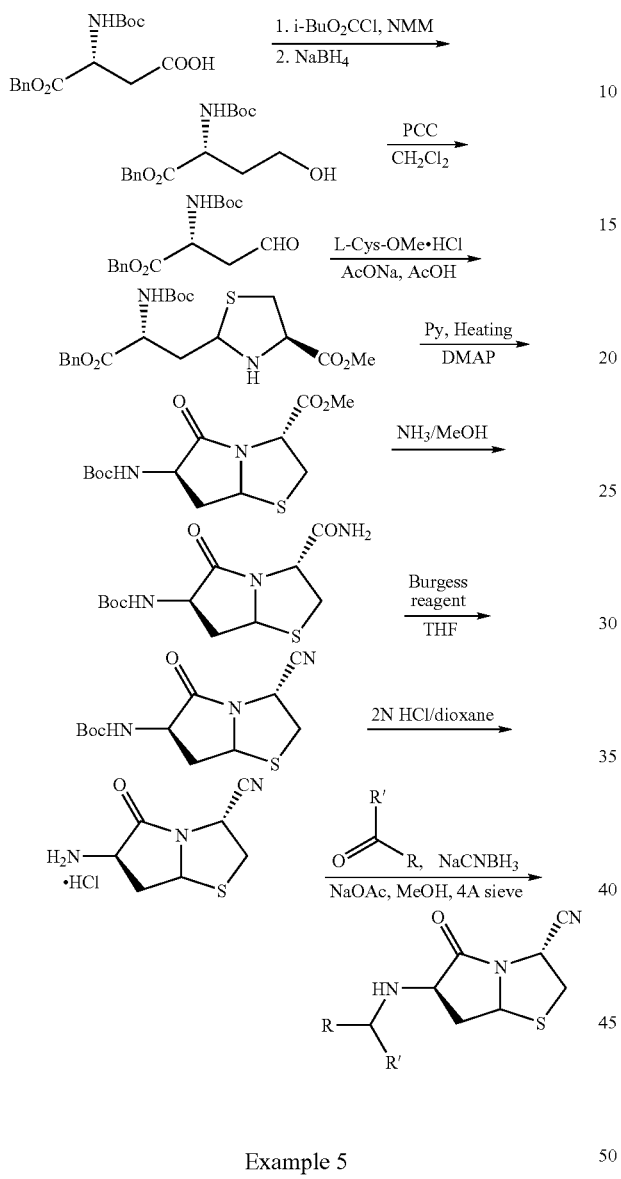
Example 5
The following compounds in Table I were prepared using the procedures illustrated above and were characterized using liquid chromatography-mass spectroscopy (LC-MS).
TABLE 1
| Compound No. | Structure | LC-MS |
|---|---|---|
| 7 | 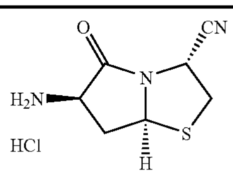 | 184(M + 1)(100), 202(78) |
| 20 | 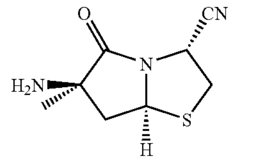 | 315(M + 1)(15), 337(100) |
| 21 | 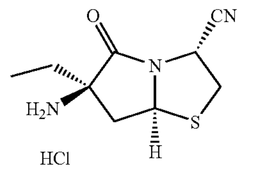 | 211.9(M + 1)(100) |
| 22 | 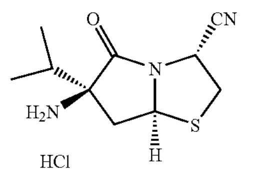 | 225.8(M + 1)(100) |
| 23 | 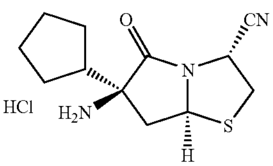 | 252.9(M + 1)(100) |
| 24 | 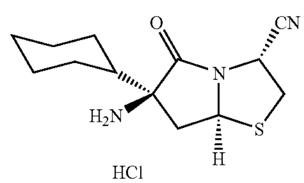 | 266(M + 1)(100) |
| 25 | 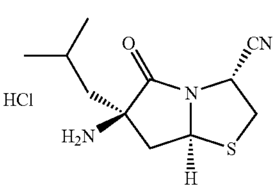 | 239.9(M + 1)(100) 233(18) |
| 26 | 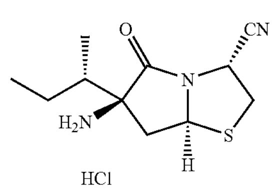 | 239.9(M + 1)(100) |
| 27 | 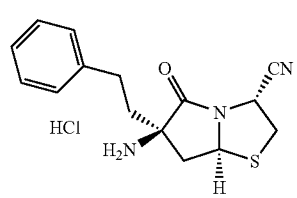 | 287.8(M + 1)(100) |

TABLE 1-continued

| Compound No. | Structure | LC-MS |
|---|---|---|
| 28 | 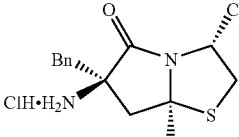 | 274.9(M + 1)(100) |
| 29 | 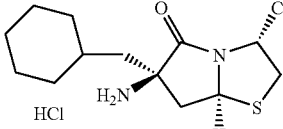 | 279.9(M + 1)(100) |
| 30 | 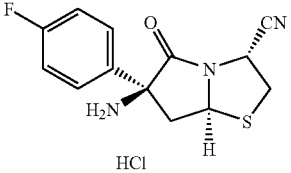 | 278(M + 1)(100) |
| 31 | 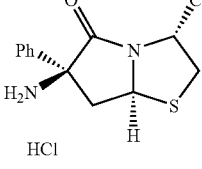 | 260(M + 1)(100) |
| 32 | 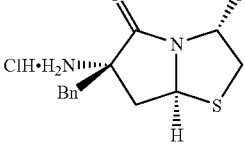 | 274(M + 1)(100) |
| 33 | 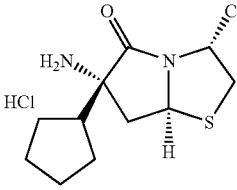 | 252(M + 1)(100) |
| 34 | 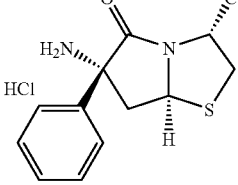 | 260(M + 1)(100) |

Example 6

Methods For Measuring DPP-IV Activity

The following methods can be used to measure the activities of the compounds of the invention which inhibit the enzymatic activity of DPP-IV. The compounds of the invention are tested for their ability to inhibit the enzyme activity of purified DPP-IV. Briefly, the activity of DPP-IV is measured in vitro by its ability to cleave the synthetic substrate Gly-Pro-AMC. Cleavage of Gly-Pro-AMC by DPP-IV liberates the product AMC (7-amino-4-methyl coumarin), whose rate of appearance is directly proportional to the enzyme activity. Inhibition of the enzyme activity by specific enzyme inhibitors slows down the generation of AMC. Stronger interaction between an inhibitor and the enzyme results in a slower rate of generation of AMC. Thus, the degree of inhibition of the rate of accumulation of AMC is a direct measure of the strength of enzyme inhibition. The accumulation of AMC is measured fluorometrically. The inhibition constant, Ki, or the $IC_{50}$ (concentration of test compound at which 50% of the enzyme activity is inhibited) for each compound is determined by incubating fixed amounts of enzyme with several different concentrations of inhibitor and substrate.

Thus, DPP-IV enzyme activity is determined by a fluorometric assay with the substrate Gly-Pro-AMC which is cleaved by DPP-IV to release the fluorescent AMC leaving group. Free AMC (7-amino-4-methyl coumarin) was measured using an excitation wavelength of 380 nm and an emission wavelength of 460 nm with a Victor-II fluorescent reader. Stock solutions of DPP-IV (1 ng/µl, pH 8.0) and Gly-Pro-AMC substrate (400 µM) in 25 mM Tris buffer (pH 8.0) are prepared separately. Test compounds are dissolved in DMSO or in 50 mM glycine buffer (pH 3.0). The assay is performed by diluting the DPP-IV stock (10 µl) into 25 mM Tris buffer (77.5 µl) followed by addition of test compound (2.5 µl) at 26° C. After 10-minutes substrate is added (10 µl) and allowed to react for 20-minutes at 26° C. before free AMC is measured. $IC_{50}$ values are determined in triplicate, using a minimum of six different inhibitor concentrations. $IC_{50}$ values are calculated using Nonlinear Regression Analysis (GraphPad, Prism, San Diego, Calif.).

The purification of porcine DPP-IV and the enzyme assay under steady state conditions are described in (1) Rahfeld, J. Schutkowski, M., Faust, J., Neubert., Barth, A., and Heins, J. (1991) Biol. Chem. Hoppe-Seyler, 372, 313-318; and (2) Nagatsu, T., Hino, M., Fuyamada, H., Hayakawa, T., Sakakibara, S., Nakagawa, Y., and Takemoto, T. (1976) Anal. Biochem., 74, 466-476, respectively. DPP-IV is also commercially available from, e.g., Research Diagnostics.

The final compounds of Examples 1-3 were tested in vitro as inhibitors of DPP-IV as described herein and each displayed an $IC_{50}$ and/or Ki of 100 µM or less.

Example 7

Methods for Measuring Activity of DPP-VII, DPP-VIII, DPP-IX, and FAP

Materials. S9 insect cells and Sf-900 II SFM media were from Invitrogen. Anti-FLAG M2 immunoaffinity gel was from Sigma. Gly-Pro-AMC, Lys-Pro AMC, and Ala-Pro AMC were from Enzyme Systems. $IC_{50}$ calculations were performed by non-linear regression analysis using Prism software (GraphPad).

Preparation of DPP-VII DPP-VIII DPP-IX, and FAP baculovirus constructs. The full length cDNAs for human DPP-VII, DPP-VIII, DPP-IX, and FAP were obtained from Open Biosystems. The cDNAs were cloned into the pFastBac vector with the addition of an N-terminal FLAG tag on DPP-VII, C-terminal 6x His tags on DPP-VIII and DPP-IX, and an N-terminal 6x His tag on FAP (Sun 2002, Qi 2003, and Chen 2004). Baculovirus was prepared using the Bac-to-Bac Baculovirus Expression System (Invitrogen). The cDNAs in the final baculovirus constructs were sequence verified.

Baculovirus expression. S9 cells were grown to mid log phase at 27C with shaking at 125 RPM and then adjusted to 2×10E6/ml just prior to baculovirus infection. Infection with DPP-VII, DPP-VIII, DPP-IX, and FAP baculoviral constructs were all performed at an MOI of 4. The infected cells were grown for 48 hours and the cell pellets harvested and frozen until purification. DPP-VII was purified using anti-FLAG immunoaffinity gel according to the manufacturer's instructions. DPP-VIII, DPP-IX, and FAP were purified using a B-PER 6× His Fusion Protein Column Purification Kit from Pierce.

$C_{50}$ assay. Recombinant DPPs were diluted in reaction buffer to give fluorescence values of 5000-20000 counts in the "enzyme only wells" 20 min after addition of substrate at 27° C. Reaction buffers were 25 mM (2-(4-Morpholino)-Ethane Sulfonic Acid), pH 5.5 for DPP-VII, 25 mM Tris, pH 8, 1% Triton X-100, 100 mM NaCl for DPP-VIII, and 25 mM Tris pH 8 for DPP-IX and FAP. Test wells in a 96-well microtiter plate contained 88 uL of diluted DPP and 2.5 ul of titrated compound in 50 mM glycine, pH 2.6. "Enzyme only" wells contained 88 uL of diluted DPP and 2.5 ul of glycine buffer. "No enzyme" wells contained 88 uL of reaction buffer without DPP and 2.5 ul of glycine buffer. All assays were done in triplicate. The plate was incubated at 27° C. for 10 min and then cooled on ice for 10 min. Ten microliters of substrate diluted in reaction buffer (40 uM final concentration) without Triton or NaCl were then added to all wells followed by incubation at 27C for 20 min. Substrates were Lys-Pro AMC for DPP-VII, and Ala-Pro AMC for DPP-VIII, DPP-IX, and FAP. Fluorescence in each well was measured at settings of 380/460 nm.

Compounds of the invention were tested for inhibition of DPP-IV according to Example 4 and DPP-VII, VIII, IX and FAP according to the present methods. Results are shown in Table 2.

TABLE 2

| Compound No. | Selectivity Ratios* | | | |
|---|---|---|---|---|
| | DPP-VII | DPP-VIII | DPP-IX | FAP |
| 7 | C | B | A | C |
| 20 | B | B | A | B |
| 21 | C | B | A | C |
| 22 | C | B | A | C |
| 23 | B | A | A | C |
| 24 | B | A | A | C |
| 25 | A | B | A | C |
| 26 | B | B | A | C |
| 27 | A | A | A | B |
| 28 | B | B | B | B |
| 29 | A | A | A | C |
| 30 | B | B | A | B |
| 31 | C | C | B | C |
| 32 | C | B | A | C |
| 33 | B | B | A | B |
| 34 | C | B | A | C |

*Selectivity ratios: A ≦ 10; 10 < B < 100; C ≧ 100.

As shown in Table 2, compounds of the invention demonstrate unexpected selectivity towards the other dipeptidyl peptidases while maintaining potency against DPP-IV. In particular each of the compounds show excellent selectivity for DPP-IV relative to DPP-VIII. As has been shown by others (Webber A E, et. al. 64$^{th}$ American Diabetes Association Conference 2004, Poster #1415), inhibition of DPP-VIII (and possibly DPP-IX) has been tied to debilitating side-effects in animal studies. Therefore, compounds of the invention are expected to show a much lower incidence of DPP-VIII mediated side-effects in vivo.

While the invention has been described and exemplified in sufficient detail for those skilled in this art to make and use it, various alternatives, modifications, and improvements will be apparent to those skilled in the art without departing from the spirit and scope of the claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

Other embodiments are set forth within the following claims.

What is claimed is:

1. A compound selected from the group consisting of:
   6-Amino-5-oxo-hexahydro-pyrrolo[2,1-b]thiazole-3-carbonitrile hydrochloride,
   6-Amino-6-methyl-5-oxo-hexahydro-pyrrolo[2,1-b]thiazole-3-carbonitrile,
   6-Amino-6-ethyl-5-oxo-hexahydro-pyrrolo[2,1-b]thiazole-3-carbonitrile hydrochloride,
   6-Amino-6-isopropyl-5-oxo-hexahydro-pyrrolo[2,1-b]thiazole-3-carbonitrile hydrochloride,
   6-Amino-6-cyclopentyl-5-oxo-hexahydro-pyrrolo[2,1-b]thiazole-3-carbonitrile hydrochloride,
   6-Amino-6-cyclohexyl-5-oxo-hexahydro-pyrrolo[2,1-b]thiazole-3-carbonitrile hydrochloride,
   6-Amino-6-isobutyl-5-oxo-hexahydro-pyrrolo[2,1-b]thiazole-3-carbonitrile hydrochloride,
   6-Amino-6-sec-butyl-5-oxo-hexahydro-pyrrolo[2,1-b]thiazole-3-carbonitrile hydrochloride,
   6-Amino-5-oxo-6-phenethyl-hexahydro-pyrrolo[2,1-b]thiazole-3-carbonitrile hydrochloride,
   6-Amino-6-benzyl-5-oxo-hexahydro-pyrrolo[2,1-b]thiazole-3-carbonitrile hydrochloride,
   6-Amino-6-cyclohexylmethyl-5-oxo-hexahydro-pyrrolo[2,1-b]thiazole-3-carbonitrile hydrochloride,
   6-Amino-6-(4-fluoro-phenyl)-5-oxo-hexahydro-pyrrolo[2,1-b]thiazole-3-carbonitrile hydrochloride, and
   6-Amino-5-oxo-6-phenyl-hexahydro-pyrrolo[2,1-b]thiazole-3-carbonitrile.

2. A pharmaceutical composition comprising the compound of claim 1 and at least one pharmaceutically acceptable carrier or diluent.

3. The compound of claim 1, wherein the compound is 6-Amino-5-oxo-hexahydro-pyrrolo[2,1-b]thiazole-3-carbonitrile hydrochloride.

4. The compound of claim 1, wherein the compound is 6-Amino-6-methyl-5-oxo-hexahydro-pyrrolo[2,1-b]thiazole-3-carbonitrile.

5. The compound of claim 1, wherein the compound is 6-Amino-6-ethyl-5-oxo-hexahydro-pyrrolo[2,1-b]thiazole-3-carbonitrile hydrochloride.

6. The compound of claim 1, wherein the compound is 6-Amino-6-isopropyl-5-oxo-hexahydro-pyrrolo[2,1-b]thiazole-3-carbonitrile hydrochloride.

7. The compound of claim 1, wherein the compound is 6-Amino-6-cyclopentyl-5-oxo-hexahydro-pyrrolo[2,1-b]thiazole-3-carbonitrile hydrochloride.

8. The compound of claim 1, wherein the compound is 6-Amino-6-cyclohexyl-5-oxo-hexahydro-pyrrolo[2,1-b]thiazole-3-carbonitrile hydrochloride.

9. The compound of claim 1, wherein the compound is 6-Amino-6-isobutyl-5-oxo-hexahydro-pyrrolo[2,1-b]thiazole-3-carbonitrile hydrochloride.

10. The compound of claim 1, wherein the compound is 6-Amino-6-sec-butyl-5-oxo-hexahydro-pyrrolo[2,1-b]thiazole-3-carbonitrile hydrochloride.

11. The compound of claim 1, wherein the compound is 6-Amino-5-oxo-6-phenethyl-hexahydro-pyrrolo[2,1-b]thiazole-3-carbonitrile hydrochloride.

12. The compound of claim 1, wherein the compound is 6-Amino-6-benzyl-5-oxo-hexahydro-pyrrolo[2,1-b]thiazole-3-carbonitrile hydrochloride.

13. The compound of claim 1, wherein the compound is 6-Amino-6-cyclohexylmethyl5oxo-hexahydro-pyrrolo[2,1-b]thiazole-3carbonitrile hydrochloride.

14. The compound of claim 1, wherein the compound is 6-Amino-6-(4-fluoro-phenyl)-5-oxo-hexahydro-pyrrolo[2,1-b]thiazole-3-carbonitrile hydrochloride.

15. The compound of claim 1, wherein the compound is 6-Amino-5-oxo-6-phenyl-hexahydro-pyrrolo[2,1-b]thiazole-3-carbonitrile hydrochloride.

16. A compound selected from the group consisting of compounds (i)-(xvi) and pharmaceutically acceptable salts thereof:

(i)
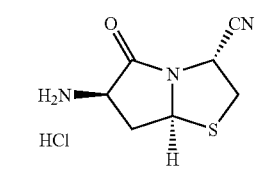

(ii)
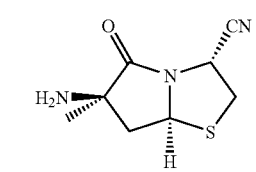

(iii)
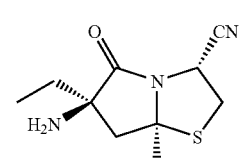

(iv)
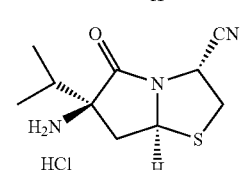

(v)
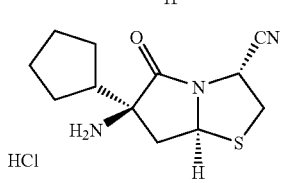

-continued (vi)
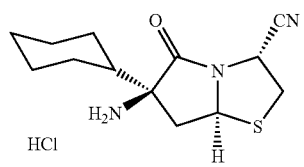

(vii)
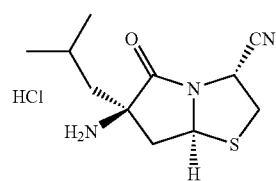

(viii)
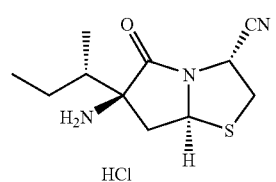

(ix)
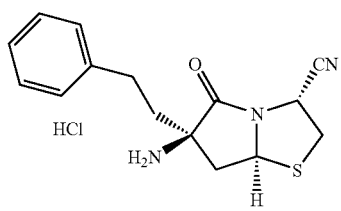

(x)
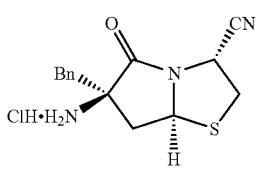

(xi)
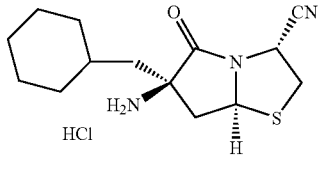

(xii)
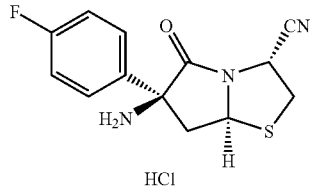

(xiii)
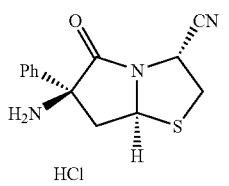

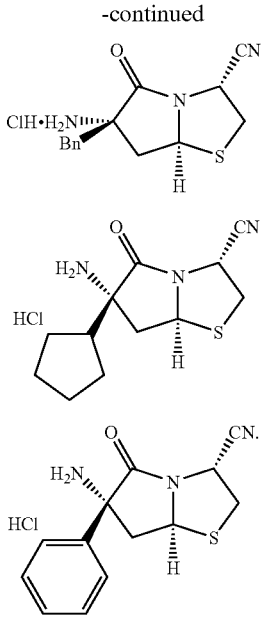

17. The compound of claim 16, wherein the compound is compound (i) or a pharmaceutically acceptable salt thereof.

18. The compound of claim 16, wherein the compound is compound (ii) or a pharmaceutically acceptable salt thereof.

19. The compound of claim 16, wherein the compound is compound (iii) or a pharmaceutically acceptable salt thereof.

20. The compound of claim 16, wherein the compound is compound (iv) or a pharmaceutically acceptable salt thereof.

21. The compound of claim 16, wherein the compound is compound (v) or a pharmaceutically acceptable salt thereof.

22. The compound of claim 16, wherein the compound is compound (vi) or a pharmaceutically acceptable salt thereof.

23. The compound of claim 16, wherein the compound is compound (vii) or a pharmaceutically acceptable salt thereof.

24. The compound of claim 16, wherein the compound is compound (viii) or a pharmaceutically acceptable salt thereof.

25. The compound of claim 16, wherein the compound is compound (ix) or a pharmaceutically acceptable salt thereof.

26. The compound of claim 16, wherein the compound is compound (x) or a pharmaceutically acceptable salt thereof.

27. The compound of claim 16, wherein the compound is compound (xi) or a pharmaceutically acceptable salt thereof.

28. The compound of claim 16, wherein the compound is compound (xii) or a pharmaceutically acceptable salt thereof.

29. The compound of claim 16, wherein the compound is compound (xiii) or a pharmaceutically acceptable salt thereof.

30. The compound of claim 16, wherein the compound is compound (xiv) or a pharmaceutically acceptable salt thereof.

31. The compound of claim 16, wherein the compound is compound (xv) or a pharmaceutically acceptable salt thereof.

32. The compound of claim 16, wherein the compound is compound (xvi) or a pharmaceutically acceptable salt thereof.

33. A pharmaceutical composition comprising the compound of claim 1 and at least one compound selected from the group consisting of metformin, pioglitazone, a sulfonyl urea, and a thiazolidinedione.

34. A pharmaceutical composition comprising the compound of claim 16 and at least one compound selected from the group consisting of metformin, pioglitazone, a sulfonyl urea, and a thiazolidinedione.

* * * * *